US006201020B1

United States Patent
Zhang et al.

(10) Patent No.: US 6,201,020 B1
(45) Date of Patent: Mar. 13, 2001

(54) ORTHO-DIPHENOL COMPOUNDS, METHODS AND PHARMACEUTICAL COMPOSITIONS FOR INHIBITING PARP

(75) Inventors: Jie Zhang, Ellicott; Larisa E. Serdyuk, Baltimore; Jia-He Li, Cockevsville, all of MD (US)

(73) Assignee: Guilford Pharmaceuticals, Inc., Baltimore, MD (US)

( * ) Notice: Subject to any disclaimer, the term of this patent is extended or adjusted under 35 U.S.C. 154(b) by 0 days.

(21) Appl. No.: 09/224,294

(22) Filed: Dec. 31, 1998

(51) Int. Cl.[7] .................... A61K 31/235; C07C 69/035; C07C 69/76

(52) U.S. Cl. .................... 514/544; 514/532; 514/538; 514/546; 514/551; 560/15; 560/29; 560/35; 560/64; 560/65; 560/73; 560/100; 560/103; 560/109; 560/125

(58) Field of Search .................... 558/392, 396; 560/1, 15, 20, 19, 35, 25, 63, 64, 65, 100, 103, 109, 125, 56, 73, 121, 122, 123, 124; 514/529, 532, 538, 544, 546, 551

(56) References Cited

U.S. PATENT DOCUMENTS

| 3,904,671 | 9/1975 | Minatoya et al. . |
| 5,177,075 | 1/1993 | Suto et al. . |
| 5,587,384 | 12/1996 | Zhang et al. . |
| 5,589,483 | 12/1996 | West .................... 514/310 |
| 5,756,510 | 5/1998 | Griffin et al. . |

OTHER PUBLICATIONS

Kourounakis et al, "Synthesis and evaluation of brain-targeted chemical delivery systems for the neurotrophomodulator 4-methylcatechol", 126(17):942 (1997), Chemical Abstracts No. 229493f.

Banasik et al., "Inhibitors and Activators of ADP-Ribosylation Reactions", *Molec. Cell. Biochem.*, 138:185–97 (1994).

Banasik et al., "Specific Inhibitors of Poly(ADP-Ribose) Synthetase and Mono(ADP-Ribosyl) transferase", *Journal of Biological Chemistry*, 267(3):1569–75 (Jan. 25, 1992).

(List continued on next page.)

*Primary Examiner*—Deborah C. Lambkin
*Assistant Examiner*—Ebenezer Sackey
(74) *Attorney, Agent, or Firm*—Nixon & Vanderhye, P.C.

(57) ABSTRACT

This invention relates to compounds, pharmaceutical compositions, and methods of using compounds of the formula:

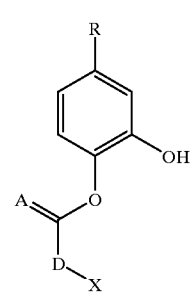

I

A is O or S;

R is $C_1$–$C_{10}$ straight or branched chain alkyl, $C_2$–$C_{10}$ straight or branched chain alkenyl, $C_2$–$C_{10}$ straight or branched chain alkynyl, aryl, heteroaryl, carbocycle, or heterocycle;

D is a bond, or a $C_1$–$C_3$ straight or branched chain alkyl, $C_2$–$C_3$ straight or branched chain alkenyl, $C_2$–$C_3$ straight or branched chain alkynyl, wherein any of the carbon atoms of said alkyl, alkenyl, or alkynyl of D are optionally replaced with oxygen, nitrogen, or sulfur; and X is aryl, heteroaryl, carbocycle, or heterocycle.

31 Claims, 2 Drawing Sheets

OTHER PUBLICATIONS

Bauer et al. "Modification of Growth Related Enzymatic Pathways and Apparent Loss of Tumorigenicity of a ras–transformed Bovine Endothelial Cell Line by Treatment with 5–Iodo–6–amino–1,2–benzopyrone (INH$_2$BP)", *Intl. J. Oncol.,* 8:239–52 (1996).

Beckman et al., "Pathological Implications of Nitric Oxide, Superoxide and Peroxynitrite Formation", *Biochemical Society Transactions,* 21:330–334 (1993).

Cosi et al., Poly(ADP–Ribose) Polymerase (PARP) Revisited. A New Role for an Old Enzyme: PARP Involvement in Neurodegeneration and PARP Inhibitors as Possible Neuroprotective Agents, *Ann. N. Y. Acad. Sci.,* 825:366–79 (1997).

Cosi et al., "Poly(ADP–Ribose) Polymerase Protect Against MPTP–induced Depletions of Striatal Dopamine and Cortical Noradrenaline in C57B1/6 Mice," *Brain Res.,* 729:264–69 (1996).

Cristovao et al., "Effect of a Poly(ADP–Ribose)Polermerase Inhibitor on DNA Breakage and Cytotoxicity Induced by Hydrogen Peroxide and g–Radiation," *Terato., Carcino., and Muta.,* 16:219–27 (1996).

Cuzzocrea, "Role of Peroxynitrite and Activation of Poly-(ADP–Ribose) Synthetase in the Vascular Failure Induced by Zymosan–activated Plasma," *Brit. J. Pharm.,* 122:493–503 (1997).

Dawson et al., "Mechanisms of Nitric Oxide–mediated Neurotoxicity in Primary Brain Cultures", *J. Neurosci.,* 13:6, 2651–61 (1993).

Dawson et al., "Nitric Oxide Mediates Glutamate Neurotoxicity in Primary Cortical Cultures," *Proc. Natl. Acad. Sci. USA,* 88:6368–71 (1991).

Dawson et al., "Protection of the Brain from Ischemia," *Cerebrovascular Disease,* 319–25 (H. Hunt Batjer ed., 1997).

Dawson et al., "Resistance to Neurotoxicity in Cortical Cultures from Neuronal Nitric Oxide Synthase–Deficient Mice", *J. Neurosci.,* 16:8, 2479–87 (1996).

Endres et al., "Ischemic Brain Injury is Mediated by the Activation of Poly(ADP–Ribose) Polymerase," *J. Cerebral Flood Flow Metabol.,* 17(11):1143–51 (1997).

Heller et al., "Inactivation of the Poly(ADP–Ribose)Polymerase Gene Affects Oxygen Radical and Nitric Oxide Toxicity in Islet Cells," *J. Biol. Chem.,* 270:19, 11176–80 (May 1995).

Huang et al., "Effects of Cerebral Ischemia in Mice Deficient in Neuronal Nitric Oxide Synthase", *Science,* 265:1883–1885 (1994).

Hughes et al., "Induction of T Helper Cell Hyporesponsiveness in an Experimental Model of Autoimmunity by Using Nonmitogenic Anti–CD3 Monoclonal Antibody", *J. Immuno.,* 153:3319–25 (1994).

Iadecola, "Bright and Dark Sides of Nitric Oxide in Ischemic Brain Injury", *Trends Neurosci.* 20:3, 132–139 (1997).

Milam et al., "Inhibitors of Poly(Adenosine Diphosphate–Ribose) Synthesis: Effect on Other Metabolic Processes", *Science,* 223:589–91 (1984).

Purnell et al., "Novel Inhibitors of Poly(ADP–Ribose) Synthase", *Biochem. J.,* 185, 775–77 (1980).

Salzman et al., "Role of Peroxynitrite and Poly(ADP–Ribose)Synthase Activation Experimental Colitis," *Japanese J. Pharm.,* 75, Supp. I:15 (1997).

Southan et al., "Spontaneous Rearrangement of Aminoalkylithioureas into Mercaptoalkylguanidines, a Novel Class of Nitric Oxid Synthase Inhibitors with Selectivity Towards the Inducible Isoform", *Br. J. Pharm.,* 117:619–32 (1996).

M.J. Suto et al., "Dihydroisoquinolinones: The Design and Sythesis of a New Series of Potent Inhibitors of Poly(ADP–Ribose) Polymerase", *Anti–Cancer Drug Design,* vol. 7, pp. 107–17 (1991).

Szabó et al., "DNA Strand Breakage, Activation of Poly-(ADP–Ribose) Synthetase, and Cellular Energy Depletion are Involved in the Cytotoxicity in Macrophages and Smooth Muscle Cells Exposed to Peroxynitrite", *Proc. Natl. Acad. Sci. USA,* 93:1753–58 (1996).

Szabó et al., "Mercaptoethylguanidine and Guanidine Inhibitors of Nitric Oxide Synthase React with Peroxynitrite and protect Against Peroxynitrite–induced Oxidative Damage", *J. Biol. Chem.,* 272:9030–36 (1997).

Szabó et al., "Protective Effects of an Inhibitor of Poly(ADP–Ribose) Synthetase in Collagen–Induced Arthritis", *Japanese J. Pharm.,* 75, Supp. I:102 (1997).

Thiemermann et al., "Inhibition of the Activity of Poly(ADP Ribose) Synthetase Reduces Ischemia–Reperfusion Injury in the Heart and Skeletal Muscle",*Proc. Natl. Acad. Sci. USA,* 94:679–83 (1997).

Wallis et al., "Neuroprotection Against Nitric Oxide Injury with Inhibitors of ADP–ribosylation," *NeuroReport,* 5:3, 245–48 (1993).

Wallis et al., Traumatic Neuroprotection with Inhibitors of Nitric Oxide and ADP–ribosylation, *Brain Res.,* 710:169–77 (1996).

Weltin et al., "Effect of 6(5H)–Phenanthridinone, an Inhibitor of Poly(ADP–ribose) Polymerase, on Cultured Tumor Cells", *Oncol. Res.,* 6:9, 399–403 (1994).

Zhang et al., "Nitric Oxide Activation of Poly(ADP–ribose) Synthetase in Neurotoxicity," *Science,* 263:687–89 (1994).

Zhang et al., "Poly(ADP–Ribose) Synthetase Activation: An Early Indicator of Neurotoxic DNA Damage," *J. Neurochem.,* 65:3, 1411–14 (1995).

Zingarelli et al., "Protective Effects of Nicotinamide Against Nitric Oxide–Mediated Delated Vascular Failure in Endotoxic Shock: Potential Involvement of PolyADP Ribosyl Synthetase," *Shock,* 5:258–64 (1996).

Banister et al., Chemical Abstract, vol. 127:80243, 1997.

Beilstein Handbook of Organic Chemistry, Reg. No. 3140506, 1998.

Buckman et al., Chemical Abstract, vol. 115:158338, 1991.

Ge et al., Chemical Abstract, vol. 125:277462, 1996.

Kyota et al., Chemical Abstract, vol. 120:95793, 1994.

Malhotra et al., Chemical Abstract, vol. 126:115554, 1996.

Marek et al., Chemical Abstract, vol. 127:81282, 1997.

Minatoya et al., Chemical Abstract, vol. 82:30602, 1978.

Minatoya et al., Chemical Abstract, vol. 84:16943, 1976.

Sakai et al., Chemical Abstract, vol. 128:36109, 1997.

Tullar et al., Chemical Abstract, vol. 85:182, 1976.

Yamaguchi et al., Chemical Abstract, vol. 125:87882, 1996.

Yoshida et al., Chemical Abstract, abstract no. 17462, 1998.

ORTHO-DIPHENOL COMPOUNDS, METHODS AND PHARMACEUTICAL COMPOSITIONS FOR INHIBITING PARP

BACKGROUND OF THE INVENTION

1. Field of the Invention

The present invention relates to inhibitors of the nucleic enzyme poly(adenosine 5'-diphospho-ribose) polymerase ["poly(ADP-ribose) polymerase" or "PARP", which is also sometimes called "PARS" for poly(ADP-ribose) synthetase or "PART" for poly (ADP-ribose) transferase]. More particularly, the invention relates to the use of PARP inhibitors to prevent and/or treat tissue damage resulting from cell damage or death due to necrosis or apoptosis, neural tissue damage resulting from ischemia and reperfusion injury, neurological disorders and neurodegenerative diseases; to prevent or treat vascular stroke; to treat or prevent cardiovascular disorders; to treat other conditions and/or disorders such as age-related macular degeneration, AIDS and other immune diseases, arthritis, atherosclerosis, cachexia, cancer, degenerative diseases of skeletal muscle involving replicative senescence, diabetes, head trauma, immune senescence, inflammatory bowel disorders (such as colitis and Crohn's disease), muscular dystrophy, osteoarthritis, osteoporosis, chronic and acute pain (such as neuropathic pain), renal failure, retinal ischemia, septic shock (such as endotoxic shock), and skin aging; to extend the lifespan and proliferative capacity of cells; to alter gene expression of senescent cells; or to radiosensitize hypoxic tumor cells.

2. Description of the Prior Art

Poly(ADP-ribose) polymerase ("PARP") is a type of enzyme located in the nuclei of cells of various organs, including muscle, heart and brain cells. Several structural variants or isoforms of PARP enzymes have been isolated in various species and tissue types, and all of these enzymes are capable of PARP activity which consists of ADP-ribosylation. Babiychuk et al., "Higher Plants Possess Two Structurally Different Poly(ADP-Ribose) Polymerases", (1998) *Plant Journal* 15:635–645. Smith et al., "Tankyrase, a Poly(ADP-Ribose) Polymerase at Human Telomeres", *Science* 282:1484–1487 (1998). These structurally-variant forms of PARP enzymes are all referred to herein as PARP. Furthermore, the compounds of the present invention would be expected to inhibit the PARP activity of any and all enzymes which can perform ADP-Ribosylation. These PARP enzymes, collectively referred to as PARP, play a physiological role in the repair of strand breaks in DNA. Once activated by damaged DNA fragments, PARP catalyzes the attachment of up to 100 ADP-ribose units to a variety of nuclear proteins, including histones and PARP itself. While the exact range of functions of PARP has not been fully established, this enzyme is thought to play a role in enhancing DNA repair.

During major cellular stresses, however, the extensive activation of PARP can rapidly lead to cell damage or death through depletion of energy stores. Four molecules of ATP are consumed for every molecule of NAD (the source of ADP-ribose) regenerated. Thus, NAD, the substrate of PARP, is depleted by massive PARP activation and, in the efforts to re-synthesize NAD, ATP may also be depleted.

It has been reported that PARP activation plays a key role in both glutamate- and NO-induced neurotoxicity, as shown by the use of PARP inhibitors to prevent such toxicity in cortical cultures in proportion to their potencies as inhibitors of this enzyme (Zhang et al., "Nitric Oxide Activation of Poly(ADP-Ribose) Synthetase in Neurotoxicity", *Science*, 263:687–89 (1994)); and in hippocampal slices (Wallis et al., "Neuroprotection Against Nitric Oxide Injury with Inhibitors of ADP-Ribosylation", *NeuroReport*, 5:3, 245–48 (1993)). The potential role of PARP inhibitors in treating neurodegenerative diseases and head trauma has thus been known. Research, however, continues to pinpoint the exact mechanisms of their salutary effect in cerebral ischemia, (Endres et al., "Ischemic Brain Injury is Mediated by the Activation of Poly(ADP-Ribose) Polymerase", *J. Cereb. Blood Flow Metabol.*, 17:1143–51 (1997)) and in traumatic brain injury (Wallis et al., "Traumatic Neuroprotection with Inhibitors of Nitric Oxide and ADP-Ribosylation, *Brain Res.*, 710:169–77 (1996)).

It has been demonstrated that single injections of PARP inhibitors have reduced the infarct size caused by ischemia and reperfusion of the heart or skeletal muscle in rabbits. In these studies, a single injection of the PARP inhibitor, 3-amino-benzamide (10 mg/kg), either one minute before occlusion or one minute before reperfusion, caused similar reductions in infarct size in the heart (32–42%). Another PARP inhibitor, 1,5-dihydroxyisoquinoline (1 mg/kg), reduced infarct size by a comparable degree (38–48%). Thiemermann et al., "Inhibition of the Activity of Poly(ADP Ribose) Synthetase Reduces Ischemia-Reperfusion Injury in the Heart and Skeletal Muscle", *Proc. Natl. Acad. Sci. USA*, 94:679–83 (1997). This finding has suggested that PARP inhibitors might be able to salvage previously ischemic heart or skeletal muscle tissue.

PARP activation has also been shown to provide an index of damage following neurotoxic insults by glutamate (via NMDA receptor stimulation), reactive oxygen intermediates, amyloid β-protein, n-methyl-4-phenyl-1,2,3, 6-tetrahydropyridine (MPTP) and its active metabolite N-methyl-4-phenylpyridine (MPP$^+$), which participate in pathological conditions such as stroke, Alzheimer's disease and Parkinson's disease. Zhang et al., "Poly(ADP-Ribose) Synthetase Activation: An Early Indicator of Neurotoxic DNA Damage",*J. Neurochem.*, 65:3, 1411–14 (1995). Other studies have continued to explore the role of PARP activation in cerebellar granule cells in vitro and in MPTP neurotoxicity. Cosi et al., "Poly(ADP-Ribose) Polymerase (PARP) Revisited. A New Role for an Old Enzyme: PARP Involvement in Neurodegeneration and PARP Inhibitors as Possible Neuroprotective Agents", *Ann. N. Y. Acad. Sci.*, 825:366–79 (1997); and Cosi et al., "Poly(ADP-Ribose) Polymerase Inhibitors Protect Against MPTP-induced Depletions of Striatal Dopamine and Cortical Noradrenaline in C57B1/6 Mice", *Brain Res.*, 729:264–69 (1996).

Neural damage following stroke and other neurodegenerative processes is thought to result from a massive release of the excitatory neurotransmitter glutamate, which acts upon the N-methyl-D-aspartate (NMDA) receptors and other subtype receptors. Glutamate serves as the predominate excitatory neurotransmitter in the central nervous system (CNS). Neurons release glutamate in great quantities when they are deprived of oxygen, as may occur during an ischemic brain insult such as a stroke or heart attack. This excess release of glutamate in turn causes over-stimulation (excitotoxicity) of N-methyl-D-aspartate (NMDA), AMPA, Kainate and MGR receptors. When glutamate binds to these receptors, ion channels in the receptors open, permitting flows of ions across their cell membranes, e.g., $Ca^{2+}$ and $Na^+$ into the cells and $K^+$ out of the cells. These flows of ions, especially the influx of $Ca^{2+}$, cause overstimulation of the neurons. The over-stimulated neurons secrete more glutamate, creating a feedback loop or domino effect which ultimately results in cell damage or death via the production of proteases, lipases and free radicals. Excessive activation of glutamate receptors has been implicated in various neurological diseases and conditions including epilepsy, stroke, Alzheimer's disease, Parkinson's disease, Amyotrophic Lateral Sclerosis (ALS), Huntington's disease, schizophrenia, chronic pain, ischemia and neuronal loss following hypoxia, hypoglycemia, ischemia, trauma, and nervous insult. Recent studies have also advanced a glutamatergic basis for compulsive disorders, particularly drug dependence. Evidence includes findings in many animal species, as well as, in cerebral cortical cultures treated with glutamate or NMDA, that glutamate receptor antagonists block neural damage following vascular stroke. Dawson et al., "Protection of the Brain from Ischemia", *Cerebrovascular Disease,* 319–25 (H. Hunt Batjer ed., 1997). Attempts to prevent excitotoxicity by blocking NMDA, AMPA, Kainate and MGR receptors have proven difficult because each receptor has multiple sites to which glutamate may bind. Many of the compositions that are effective in blocking the receptors are also toxic to animals. As such, there is no known effective treatment for glutamate abnormalities.

The stimulation of NMDA receptors, in turn, activates the enzyme neuronal nitric oxide synthase (NNOS), which causes the formation of nitric oxide (NO), which more directly mediates neurotoxicity. Protection against glutamate neurotoxicity mediated through the NMDA receptors has occurred following treatment with NOS inhibitors. See Dawson et al., "Nitric Oxide Mediates Glutamate Neurotoxicity in Primary Cortical Cultures", *Proc. Natl. Acad. Sci. USA,* 88:6368–71 (1991); and Dawson et al., "Mechanisms of Nitric Oxide-mediated Neurotoxicity in Primary Brain Cultures", *J. Neurosci.,* 13:6, 2651–61 (1993). Protection against glutamate neurotoxicity mediated through NMDA receptors can also occur in cortical cultures from mice with targeted disruption of NNOS. See Dawson et al., "Resistance to Neurotoxicity in Cortical Cultures from Neuronal Nitric Oxide Synthase-Deficient Mice", *J. Neurosci.,* 16:8, 2479–87 (1996).

It is known that neural damage following vascular stroke is markedly diminished in animals treated with NOS inhibitors or in mice with NNOS gene disruption. Iadecola, "Bright and Dark Sides of Nitric Oxide in Ischemic Brain Injury", *Trends Neurosci.,* 20:3, 132–39 (1997); and Huang et al., "Effects of Cerebral Ischemia in Mice Deficient in Neuronal Nitric Oxide Synthase", *Science,* 265:1883–85 (1994). See also, Beckman et al., "Pathological Implications of Nitric Oxide, Superoxide and Peroxynitrite Formation", *Biochem. Soc. Trans.,* 21:330–34 (1993). Either NO or peroxynitrite can cause DNA damage, which activates PARP. Further support for this is provided in Szabó et al., "DNA Strand Breakage, Activation of Poly(ADP-Ribose) Synthetase, and Cellular Energy Depletion are Involved in the Cytotoxicity in Macrophages and Smooth Muscle Cells Exposed to Peroxynitrite", *Proc. Natl. Acad. Sci. USA,* 93:1753–58 (1996).

Zhang et al., U.S. Pat. No. 5,587,384 issued Dec. 24, 1996, discusses the use of certain PARP inhibitors, such as benzamide and 1,5-dihydroxy-isoquinoline, to prevent NMDA-receptor mediated neurotoxicity and, thus, treat stroke, Alzheimer's disease, Parkinson's disease and Huntington's disease. However, it is has now been discovered that Zhang et al. may have been in error in classifying neurotoxicity as NMDA-receptor mediated neurotoxicity. Rather, the in vivo neurotoxicity present is more appropriately classified as glutamate neurotoxicity. See Zhang et al. "Nitric Oxide Activation of Poly(ADP-Ribose) Synthetase in Neurotoxicity", *Science,* 263:687–89 (1994). See also, Cosi et al., Poly(ADP-Ribose)Polymerase Inhibitors Protect Against MPTP-induced Depletions of Striatal Dopamine and Cortical Noradrenaline in C57B1/6 Mice", *Brain Res.,* 729:264–69 (1996).

It is also known that PARP inhibitors affect DNA repair generally. Cristovao et al., "Effect of a Poly(ADP-Ribose) Polymerase Inhibitor on DNA Breakage and Cytotoxicity Induced by Hydrogen Peroxide and γ-Radiation," *Terato., Carcino.,* and *Muta.,* 16:219–27 (1996), discusses the effect of hydrogen peroxide and γ-radiation on DNA strand breaks in the presence of and in the absence of 3-aminobenzamide, a potent inhibitor of PARP. Cristovao et al. observed a PARP-dependent recovery of DNA strand breaks in leukocytes treated with hydrogen peroxide.

PARP inhibitors have been reported to be effective in radiosensitizing hypoxic tumor cells and effective in preventing tumor cells from recovering from potentially lethal damage of DNA after radiation therapy, presumably by their ability to prevent DNA repair. See U.S. Pat. Nos. 5,032,617; 5,215,738; and 5,041,653.

Evidence also exists that PARP inhibitors are useful for treating inflammatory bowel disorders. Salzman et al., "Role of Peroxynitrite and Poly(ADP-Ribose)Synthase Activation Experimental Colitis," *Japanese J. Pharm.,* 75, Supp. I:15 (1997), discusses the ability of PARP inhibitors to prevent or treat colitis. Colitis was induced in rats by intraluminal administration of the hapten trinitrobenzene sulfonic acid in 50% ethanol and treated with 3-aminobenzamide, a specific inhibitor of PARP activity. Inhibition of PARP activity reduced the inflammatory response and restored the morphology and the energetic status of the distal colon. See also, Southan et al., "Spontaneous Rearrangement of Aminoalkylithioureas into Mercaptoalkylguanidines, a Novel Class of Nitric Oxide Synthase Inhibitors with Selectivity Towards the Inducible Isoform", *Br. J. Pharm.,* 117:619–32 (1996); and Szabó et al., "Mercaptoethylguanidine and Guanidine Inhibitors of Nitric Oxide Synthase React with Peroxynitrite and Protect Against Peroxynitrite-induced Oxidative Damage", *J. Biol. Chem.,* 272:9030–36 (1997).

Evidence also exists that PARP inhibitors are useful for treating arthritis. Szabó et al., "Protective Effects of an Inhibitor of Poly(ADP-Ribose)Synthetase in Collagen-Induced Arthritis," *Japanese J. Pharm.,* 75, Supp. I:102 (1997), discusses the ability of PARP inhibitors to prevent or treat collagen-induced arthritis. See also Szabó et al., "DNA Strand Breakage, Activation of Poly(ADP-Ribose) Synthetase, and Cellular Energy Depletion are Involved in the Cytotoxicity in Macrophages and Smooth Muscle Cells Exposed to Peroxynitrite," *Proc. Natl. Acad. Sci. USA,* 93:1753–58 (March 1996); Bauer et al., "Modification of Growth Related Enzymatic Pathways and Apparent Loss of Tumorigenicity of a ras-transformed Bovine Endothelial Cell Line by Treatment with 5-Iodo-6-amino-1,2-benzopyrone (INH$_2$BP)", *Intl. J. Oncol.,* 8:239–52 (1996); and Hughes et al., "Induction of T Helper Cell Hyporesponsiveness in an Experimental Model of Autoimmunity by Using Nonmitogenic Anti-CD3 Monoclonal Antibody", *J. Immuno.,* 153:3319–25 (1994).

Further, PARP inhibitors appear to be useful for treating diabetes. Heller et al., "Inactivation of the Poly(ADP-Ribose)Polymerase Gene Affects Oxygen Radical and Nitric Oxide Toxicity in Islet Cells," *J. Biol. Chem.,* 270:19, 11176–80 (May 1995), discusses the tendency of PARP to deplete cellular NAD+ and induce the death of insulin-producing islet cells. Heller et al. used cells from mice with inactivated PARP genes and found that these mutant cells did not show NAD+ depletion after exposure to DNA-damaging radicals. The mutant cells were also found to be more resistant to the toxicity of NO.

Further still, PARP inhibitors have been shown to be useful for treating endotoxic shock or septic shock. Zingarelli et al., "Protective Effects of Nicotinamide Against Nitric Oxide-Mediated Delayed Vascular Failure in Endotoxic Shock: Potential Involvement of PolyADP Ribosyl Synthetase," *Shock*, 5:258–64 (1996), suggests that inhibition of the DNA repair cycle triggered by poly(ADP ribose) synthetase has protective effects against vascular failure in endotoxic shock. Zingarelli et al. found that nicotinamide protects against delayed, NO-mediated vascular failure in endotoxic shock. Zingarelli et al. also found that the actions of nicotinamide may be related to inhibition of the NO-mediated activation of the energy-consuming DNA repair cycle, triggered by poly(ADP ribose) synthetase. See also, Cuzzocrea, "Role of Peroxynitrite and Activation of Poly(ADP-Ribose) Synthetase in the Vascular Failure Induced by Zymosan-activated Plasma," *Brit. J. Pharm.*, 122:493–503 (1997).

Yet another known use for PARP inhibitors is treating cancer. Suto et al., "Dihydroisoquinolinones: The Design and Synthesis of a New Series of Potent Inhibitors of Poly(ADP-Ribose) Polymerase", *Anticancer Drug Des.*, 7:107–17 (1991), discloses processes for synthesizing a number of different PARP inhibitors. In addition, Suto et al., U.S. Pat. No. 5,177,075, discusses several isoquinolines used for enhancing the lethal effects of ionizing radiation or chemotherapeutic agents on tumor cells. Weltin et al., "Effect of 6(5H)-Phenanthridinone, an Inhibitor of Poly (ADP-ribose) Polymerase, on Cultured Tumor Cells", *Oncol. Res.*, 6:9, 399–403 (1994), discusses the inhibition of PARP activity, reduced proliferation of tumor cells, and a marked synergistic effect when tumor cells are co-treated with an alkylating drug.

Still another use for PARP inhibitors is the treatment of peripheral nerve injuries, and the resultant pathological pain syndrome known as neuropathic pain, such as that induced by chronic constriction injury (CCI) of the common sciatic nerve and in which transsynaptic alteration of spinal cord dorsal horn characterized by hyperchromatosis of cytoplasm and nucleoplasm (so-called "dark" neurons) occurs. See Mao et al., *Pain*, 72:355–366 (1997).

PARP inhibitors have also been used to extend the lifespan and proliferative capacity of cells including treatment of diseases such as skin aging, Alzheimer's disease, atherosclerosis, osteoarthritis, osteoporosis, muscular dystrophy, degenerative diseases of skeletal muscle involving replicative senescence, age-related macular degeneration, immune senescence, AIDS, and other immune diseases; and to alter gene expression of senescent cells. See WO 98/27975.

Large numbers of known PARP inhibitors have been described in Banasik et al., "Specific Inhibitors of Poly (ADP-Ribose) Synthetase and Mono(ADP-Ribosyl)-Transferase", *J. Biol. Chem.*, 267:3, 1569–75 (1992), and in Banasik et al., "Inhibitors and Activators of ADP-Ribosylation Reactions", *Molec. Cell. Biochem.*, 138:185–97 (1994).

However, the approach of using these PARP inhibitors in the ways discussed above has been limited in effect. For example, side effects have been observed with some of the best-known PARP inhibitors, as discussed in Milam et al., "Inhibitors of Poly(Adenosine Diphosphate-Ribose) Synthesis: Effect on Other Metabolic Processes", *Science*, 223:589–91 (1984). Specifically, the PARP inhibitors 3-aminobenzamide and benzamide not only inhibited the action of PARP but also were shown to affect cell viability, glucose metabolism, and DNA synthesis. Thus, it was concluded that the usefulness of these PARP inhibitors may be severely restricted by the difficulty of finding a dose that will inhibit the enzyme without producing additional metabolic effects.

The inventors have now discovered that select orthodiphenol compounds can inhibit PARP activity and can treat or prevent tissue damage resulting from cell damage or death due to necrosis or apoptosis and/or can ameliorate neural tissue damage, including that following focal ischemia and reperfusion injury. Generally, inhibition of PARP activity spares the cell from energy loss, preventing irreversible depolarization of the neurons and, thus, provides neuroprotection. While not wishing to be bound thereby, it is thought that PARP activation may play a common role in still other excitotoxic mechanisms, perhaps as yet undiscovered, in addition to the production of free radicals and NO.

Certain related compounds have been disclosed for medical treatments and other uses. However, these compounds are structurally distinguishable and directed to uses which emphasize their toxic characteristics. Compounds that are used primarily as synthetic intermediates in the preparation of compounds for: treating hyperlipemia in U.S. Pat. No. 5,719,303 to Yoshida et al. "Phosphinic Acid Derivatives"; treating plant nepovirus in "Inhibition of Tomato Ringspot Virus by Flavenoids", by Malhotra et al, (1996) *Phytochem.* 43:1271–1276; inhibiting fibrosis in Japanese Patent 92JP-0098635 to Kyota et al. "Fibrosis-inhibiting Agents Containing Gallate Esters"; treatment of hypertension in European Patent 86EP-194046 to Hargreaves et al. "Dihydropyridine Alkanolamines and Their Use"; bronchodilation in U.S. Pat. 4,336,400 to Minatoya et al. "3-(Hydroxy or Hydroxymethyl)-4-Hydroxy-alpha (Aminomethyl)Benzyl Alcohols and Methods of Use"; treating snakebite in U.S. Pat. No. 4,124,724 to Agoro, "Crystalline Caffeic Acid Derivatives and Compositions for Treating Snakebite"; and bronchodilation in "Esters of N-tert-butylarterenol: Long-acting New Bronchodilators with Reduced Cardiac Effects", by Tullar et al, (1976) *J. Med. Chem.* 19:834–838.

Other related, but structurally distinct compounds for unrelated uses include: PCT Publication WO9720944 by Banister et al., "Melanin Production"; "(+)-Catechin: Benzoyl Protection of OH Groups and NMR Study of Products", by Marek et al, (1997) *Chem. Pap.* 51:107–110; "Decomposition of Polyurethane Foams Derived from Condensed Tannin", by Ge et al, (1996) *Mokuzai Gakkaishi* 42:776–781; "Cinnamic Acid Derivatives", Yamaguchi et al, (1996) *Sekiyu Gakkaishi* 39:273–278; Japanese Patent JP03088882 to Kanba et al., "Weather Resistant Water-Based Fluoropolymer Coating Compositions"; "A DTA Study of Phenols: III Polyhydroxyphenols and Naphthols", by Buckman et al, (1991) *J. Therm. Anal.* 37:79–94; and U.S. Pat. No. 3,904,671 to Minatoya et al. "(Aminohydroalkyl) Catechol Diesters".

Accordingly, there remains a need for compounds capable of acting as PARP inhibitors, pharmaceutical compositions containing the same and methods of using the same that produce more potent and reliable effects, particularly with respect to treatment of tissue damage resulting from cell death or damage due to necrosis or apoptosis, and less side effects.

SUMMARY OF THE INVENTION

The present invention relates to novel poly(ADP-ribose) polymerase ("PARP") inhibitors and methods for using the same including effecting a neuronal activity in an animal. As such, they may treat or prevent neural tissue damage resulting from cell damage or death due to necrosis or apoptosis, cerebral ischemia and reperfusion injury or neurodegenerative diseases in an animal; they may extend the lifespan and proliferative capacity of cells and thus be used to treat or prevent diseases associated therewith; they may alter gene expression of senescent cells; and they may radiosensitize hypoxic tumor cells. Preferably, the compounds of the invention treat or prevent tissue damage resulting from cell damage or death due to necrosis or apoptosis, and/or effect neuronal activity, either mediated or not mediated by glutamate neurotoxicity. These compounds are thought to interfere with more than the glutamate neurotoxicity and NO-mediated biological pathways. Further, the compounds of the invention can treat or prevent other tissue damage related to PARP activation.

For example, the compounds of the invention can treat or prevent cardiovascular tissue damage resulting from cardiac ischemia or reperfusion injury. Reperfusion injury, for instance, occurs at the termination of cardiac bypass procedures or during cardiac arrest when the heart, once prevented from receiving blood, begins to reperfuse.

The compounds of the present invention can also be used to extend or increase the lifespan or proliferation of cells and thus to treat or prevent diseases associated therewith and induced or exacerbated by cellular senescence including skin aging, atherosclerosis, osteoarthritis, osteoporosis, muscular dystrophy, degenerative diseases of skeletal muscle involving replicative senescence, age-related macular degeneration, immune senescence, AIDS and other immune diseases, and other diseases associated with cellular senescence and aging, as well as to alter the gene expression of senescent cells. These compounds can also be used to treat cancer and to radiosensitize hypoxic tumor cells to render the tumor cells more susceptible to radiation therapy and to prevent the tumor cells from recovering from potentially lethal damage of DNA after radiation therapy, presumably by their ability to prevent DNA repair. The compounds of the present invention can be used to prevent or treat vascular stroke; to treat or prevent cardiovascular disorders; to treat other conditions and/or disorders such as age-related macular degeneration, AIDS and other immune diseases, arthritis, atherosclerosis, cachexia, cancer, degenerative diseases of skeletal muscle involving replicative senescence, diabetes, head trauma, immune senescence, inflammatory bowel disorders (such as colitis and Crohn's disease), muscular dystrophy, osteoarthritis, osteoporosis, chronic and/or acute pain (such as neuropathic pain), renal failure, retinal ischemia, septic shock (such as endotoxic shock), and skin aging. Preferably, the compounds of the invention exhibit an $IC_{50}$ for inhibiting PARP in vitro of about 100 μM or lower, more preferably, about 25 μM or lower, more preferably, about 10 μM or lower, and most preferably, about 1 μM or lower.

Specifically, the present invention relates to a compound of formula I:

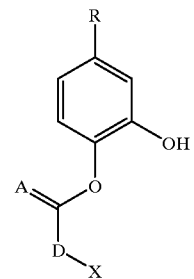

or a pharmaceutically acceptable salt, hydrate, ester, solvate, prodrug, metabolite, stereoisomer, or mixtures thereof, wherein A is O or S;

R is $C_1$–$C_{10}$ straight or branched chain alkyl, $C_2$–$C_{10}$ straight or branched chain alkenyl, $C_2$–$C_{10}$ straight or branched chain alkynyl, aryl, heteroaryl, carbocycle, or heterocycle;

D is a bond, or a $C_1$–$C_3$ straight or branched chain alkyl, $C_2$–$C_3$ straight or branched chain alkenyl, $C_2$–$C_3$ straight or branched chain alkynyl, wherein any of the carbon atoms of said alkyl, alkenyl, or alkynyl of D are optionally replaced with oxygen, nitrogen, or sulfur; and X is aryl, heteroaryl, carbocycle, or heterocycle;

wherein said alkyl, alkenyl, alkynyl, aryl, heteroaryl, carbocycle, or heterocycle of R, D, or X is optionally substituted with one or more substituents selected from hydroxy, halo, haloalkyl, thiocarbonyl, alkoxy, alkenoxy, alkylaryloxy, aryloxy, arylalkyloxy, cyano, nitro, amino, imino, alkylamino, arylamino, arylazo, arylthio, aminoalkyl, sulfhydryl, thioalkyl, alkylthio, sulfonyl, $C_1$–$C_6$ straight or branched chain alkyl, $C_2$–$C_6$ straight or branched chain alkenyl or alkynyl, aryl, aralkyl, heteroaryl, carbocycle, or heterocycle;

provided that when R is methyl, and D is a bond, then X is not phenyl, 4-nitrophenyl, 4-phenylazo-phenyl, or 3,5-dinitrophenyl; when R is a substituted benzopyran group, and D is a bond, ethenyl, or —NH—, then X is not phenyl, or 3,4,5-trihydroxyphenyl; when R is ethenyl, and D is ethenyl, then X is not 4-hydroxy-3-methoxyphenyl; when R is methyl, and D is ethenyl, then X is not 2-hydroxyphenyl; when R is 1-hydroxy-2-alkylamino-ethyl, and D is a bond, then X is not phenyl, methylphenyl, or 4-methoxyphenyl; and when R is propenyl, and D is a bond, then X is not phenyl.

A preferred embodiment of this invention is the compound of formula I, wherein R is a hydrophobic group. Another preferred embodiment of the invention is the compound of formula I, wherein R is a $C_1$–$C_{10}$ straight or branched chain alkyl.

The following are particularly preferred compounds of the present invention:

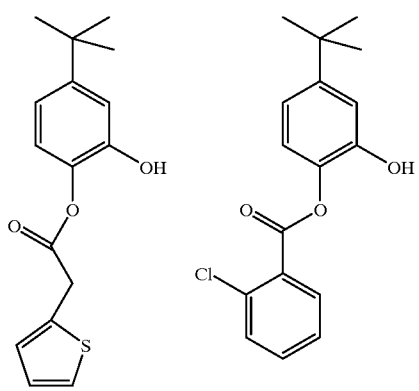
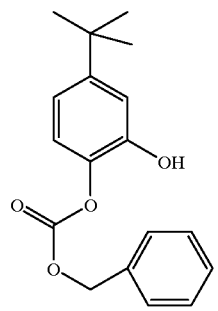

Additional preferred compounds are those of formula I as follows where A is O as exemplified by Compounds 1–51:

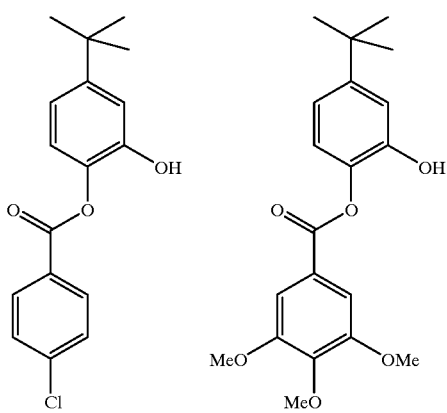
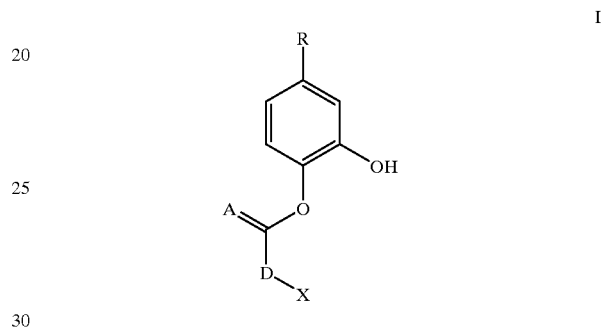

as in Table I as follows:

TABLE I where A is O

| Compound | R | D | X |
|---|---|---|---|
| 1 | methyl | bond | 4-bromophenyl |
| 2 | ethyl | bond | phenyl |
| 3 | n-propyl | bond | 3,4,5-trihydroxy-phenyl |
| 4 | i-propyl | bond | 3,4,5-trimethoxy-phenyl |
| 5 | n-butyl | bond | 3-hydroxyphenyl |
| 6 | t-butyl | bond | 4-nitro-naphthyl |
| 7 | s-butyl | bond | 3-hydroxy-naphthyl |
| 8 | pentyl | bond | benzyl |
| 9 | hexyl | bond | 4-ethylphenyl |
| 10 | heptyl | bond | 4-ethenylphenyl |
| 11 | octyl | bond | 4-quinolyl |
| 12 | nonyl | bond | 2-thiazolyl |
| 13 | decyl | bond | 3-furyl |
| 14 | 1,1,dimethyl-propyl | bond | phenyl |
| 15 | ethenyl | bond | cyclohexyl |
| 16 | prop-2-enyl | bond | 3-bromocyclohexyl |
| 17 | phenyl | bond | adamantyl |
| 18 | naphthyl | bond | 4-indolyl |
| 19 | 4-nitrophenyl | bond | 2-imidazolyl |
| 20 | 4-hydroxy-phenyl | bond | 1-naphthyl |
| 21 | 4-chlorophenyl | bond | 4-nitrophenyl |
| 22 | 4-methylphenyl | bond | 4-hydroxyphenyl |
| 23 | 4-methoxy-phenyl | bond | 3-piperidyl |
| 24 | 4-dimethyl-amino-phenyl | bond | 3,4,5-trimethyl-phenyl |
| 25 | phenyl-ethyl-phenyl | bond | 3-pyridyl |
| 26 | 4-nitro-3- | bond | 3,4,5-trifluoro- |

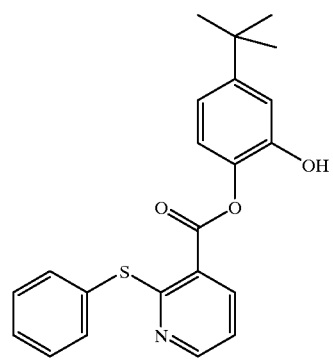
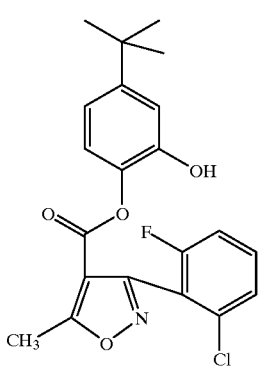

TABLE I-continued where A is O

| Compound | R | D | X |
|---|---|---|---|
| | hydroxyphenyl | | phenyl |
| 27 | 1-pyridyl | bond | 1-pyrrolidyl |
| 28 | 1-piperidyl | bond | 4-phenylazo-phenyl |
| 29 | 1-pyrrolidyl | 2-bromo-propyl | 4-amino-3-hydroxy-phenyl |
| 30 | cyclohexyl | prop-2-enyl | 3,4,5-triamino-phenyl |
| 31 | cyclopentyl | methyl | 4-hydroxyphenyl |
| 32 | adamantyl | ethyl | phenyl |
| 33 | benzyl | i-propyl | 9-anthracenyl |
| 34 | 4-hydroxy-benzyl | n-propyl | 4-pyrenyl |
| 35 | 3,4,5-trihydroxy-phenyl | 2-imino-propyl | 3-furyl |
| 36 | thiazolyl | 2-thio-propyl | 3-thiophenyl |
| 37 | 2-phenylethyl | 2-sulfonyl-propyl | 4-pyrimidinyl |
| 38 | 3-phenylpropyl | ethenyl | 4-isoquinolyl |
| 39 | 2-phenyl-ethenyl | bond | 4-sulfonylphenyl |
| 40 | 3-phenylprop-2-enyl | chloro-methyl | 4-imino-phenyl |
| 41 | 3-bromopropyl | —CH₂—N=CH— | 4-phenylethoxy-phenyl |
| 42 | 4-fluoro-n-butyl | —CH₂—S—CH₂— | 4-ethylphenoxy-phenyl |
| 43 | 3-methoxy-propyl | —CH₂—NH—CH₂— | 4-phenoxy-phenyl |
| 44 | 2-hydroxyethyl | —CH₂—O—CH₂— | 3-phenylpropyl-phenyl |
| 45 | tert-butyl | —CH₂— | 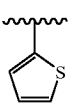 |
| 46 | tert-butyl | bond | 2-chloro-phenyl |
| 47 | tert-butyl | bond | 4-chloro-phenyl |
| 48 | tert-butyl | bond | 3,4,5-trimethoxy-phenyl |
| 49 | tert-butyl | bond | 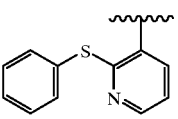 |
| 50 | tert-butyl | bond | 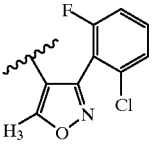 |
| 51 | tert-butyl | —O—CH₂—, X attaches directly to the CH₂ | phenyl |

Additional preferred compounds are those of formula I as follows where A is S as exemplified by Compounds 52–102:

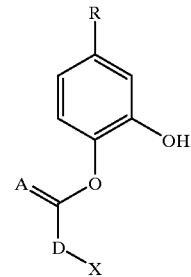

as shown in Table II as follows:

TABLE II where A is S

| Compound | R | D | X |
|---|---|---|---|
| 52 | methyl | bond | 4-bromophenyl |
| 53 | ethyl | bond | phenyl |
| 54 | n-propyl | bond | 3,4,5-trihydroxy-phenyl |
| 55 | i-propyl | bond | 3,4,5-trimethoxy-phenyl |
| 56 | n-butyl | bond | 3-hydroxyphenyl |
| 57 | t-butyl | bond | 4-nitro-naphthyl |
| 58 | s-butyl | bond | 3-hydroxy-naphthyl |
| 59 | pentyl | bond | benzyl |
| 60 | hexyl | bond | 4-ethylphenyl |
| 61 | heptyl | bond | 4-ethenylphenyl |
| 62 | octyl | bond | 4-quinolyl |
| 63 | nonyl | bond | 2-thiazolyl |
| 64 | decyl | bond | 3-furyl |
| 65 | 1,1-dimethyl-propyl | bond | phenyl |
| 66 | ethenyl | bond | cyclohexyl |
| 67 | prop-2-enyl | bond | 3-bromocyclohexyl |
| 68 | phenyl | bond | adamantyl |
| 69 | naphthyl | bond | 4-indolyl |
| 70 | 4-nitrophenyl | bond | 2-imidazolyl |
| 71 | 4-hydroxy-phenyl | bond | 1-naphthyl |
| 72 | 4-chlorophenyl | bond | 4-nitrophenyl |
| 73 | 4-methylphenyl | bond | 4-hydroxyphenyl |
| 74 | 4-methoxy-phenyl | bond | 3-piperidyl |
| 75 | 4-dimethyl-amino-phenyl | bond | 3,4,5-trimethyl-phenyl |
| 76 | phenyl-ethyl-phenyl | bond | 3-pyridyl |
| 77 | 4-nitro-3-hydroxy-phenyl | bond | 3,4,5-trifluoro-phenyl |
| 78 | 1-pyridyl | bond | 1-pyrrolidyl |
| 79 | 1-piperidyl | bond | 4-phenylazo-phenyl |
| 80 | 1-pyrrolidyl | 2-bromo-propyl | 4-amino-3-hydroxy-phenyl |
| 81 | cyclohexyl | prop-2-enyl | 3,4,5-triamino-phenyl |
| 82 | cyclopentyl | methyl | 4-hydroxyphenyl |
| 83 | adamantyl | ethyl | phenyl |
| 84 | benzyl | i-propyl | 9-anthracenyl |
| 85 | 4-hydroxy-benzyl | n-propyl | 4-pyrenyl |
| 86 | 3,4,5-trihydroxy-phenyl | 2-imino-propyl | 3-furyl |
| 87 | thiazolyl | 2-thio-propyl | 3-thiophenyl |
| 88 | 2-phenylethyl | 2-sulfonyl-propyl | 4-pyrimidinyl |

TABLE II-continued where A is S

| Compound | R | D | X |
|---|---|---|---|
| 89 | 3-phenylpropyl | ethenyl | 4-isoquinolyl |
| 90 | 2-phenyl-ethenyl | bond | 4-sulfonylphenyl |
| 91 | 3-phenylprop-2-enyl | chloro-methyl | 4-imino-phenyl |
| 92 | 3-bromopropyl | —$CH_2$—N=CH— | 4-phenylethoxy-phenyl |
| 93 | 4-fluoro-n-butyl | —$CH_2$—S—$CH_2$— | 4-ethylphenoxy-phenyl |
| 94 | 3-methoxy-propyl | —$CH_2$—NH—$CH_2$— | 4-phenoxy-phenyl |
| 95 | 2-hydroxyethyl | —$CH_2$—O—$CH_2$— | 3-phenylpropyl-phenyl |
| 96 | tert-butyl | —$CH_2$— | (thiophene) |
| 97 | tert-butyl | bond | 2-chloro-phenyl |
| 98 | tert-butyl | bond | 4-chloro-phenyl |
| 99 | tert-butyl | bond | 3,4,5-trimethoxy-phenyl |
| 100 | tert-butyl | bond | (phenyl-thio-pyridinyl) |
| 101 | tert-butyl | bond | (fluoro-chloro-phenyl-methylisoxazolyl) |
| 102 | tert-butyl | —O—$CH_2$—, X attaches directly to the $CH_2$ | phenyl |

DETAILED DESCRIPTION OF THE INVENTION

Figure 1:
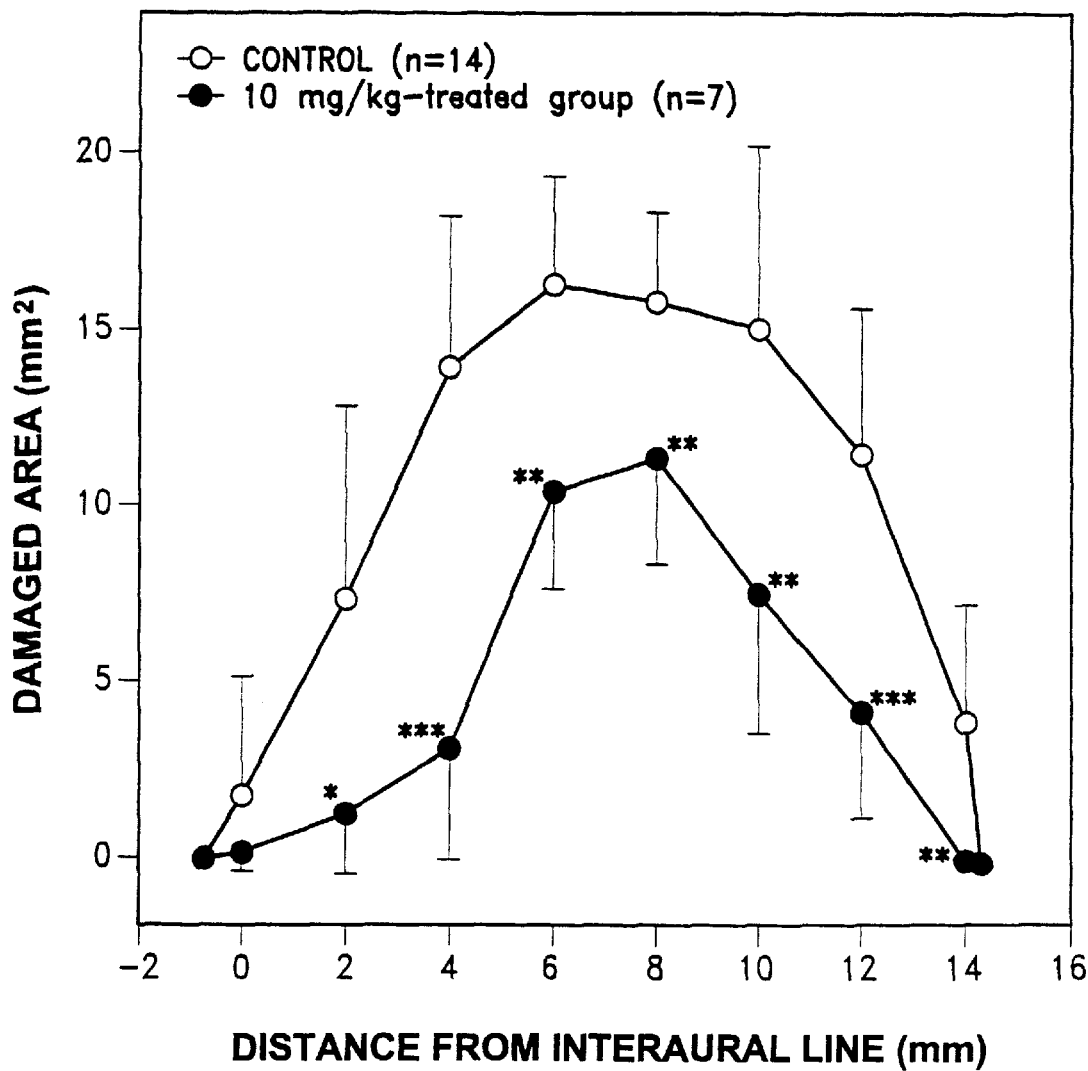
FIG. 1 shows the distribution of the cross-sectional infarct area at representative levels along the rostrocaudal axis, as measured from the interaural line in non-treated animals and in animals treated with 10 mg/kg of 3,4-dihydro-5-[4-(1-piperidinyl)-botoxyl]-1(2H)-isoquinolinone.

The present invention pertains to compounds, pharmaceutical compositions containing the same, methods of using the same, and process of making the same, wherein such compounds are useful as inhibitors of poly(ADP-ribose) polymerase (PARP). As such, they may treat or prevent neural tissue damage resulting from cell damage or death due to necrosis or apoptosis, cerebral ischemia and reperfusion injury or neurodegenerative diseases in an animal; they may extend the lifespan and proliferative capacity of cells and thus be used to treat or prevent diseases associated therewith; they may alter gene expression of senescent cells; and they may radiosensitize hypoxic tumor cells. Preferably, the compounds of the invention treat or prevent tissue damage resulting from cell damage or death due to necrosis or apoptosis, and/or effect neuronal activity, either mediated or not mediated by glutamate neurotoxicity. These compounds are thought to interfere with more than the glutamate neurotoxicity and NO-mediated biological pathways. Further, the compounds of the invention can treat or prevent other tissue damage related to PARP activation.

For example, the compounds of the invention can treat or prevent cardiovascular tissue damage resulting from cardiac ischemia or reperfusion injury. Reperfusion injury, for instance, occurs at the termination of cardiac bypass procedures or during cardiac arrest when the heart, once prevented from receiving blood, begins to reperfuse.

The compounds of the present invention can also be used to extend or increase the lifespan or proliferation of cells and thus to treat or prevent diseases associated therewith and induced or exacerbated by cellular senescence including skin aging, atherosclerosis, osteoarthritis, osteoporosis, muscular dystrophy, degenerative diseases of skeletal muscle involving replicative senescence, age-related macular degeneration, immune senescence, AIDS and other immune diseases, and other diseases associated with cellular senescence and aging, as well as to alter the gene expression of senescent cells. These compounds can also be used to treat cancer and to radiosensitize hypoxic tumor cells to render the tumor cells more susceptible to radiation therapy and to prevent the tumor cells from recovering from potentially lethal damage of DNA after radiation therapy, presumably by their ability to prevent DNA repair. The compounds of the present invention can be used to prevent or treat vascular stroke; to treat or prevent cardiovascular disorders; to treat other conditions and/or disorders such as age-related macular degeneration, AIDS and other immune diseases, arthritis, atherosclerosis, cachexia, cancer, degenerative diseases of skeletal muscle involving replicative senescence, diabetes, head trauma, immune senescence, inflammatory bowel disorders (such as colitis and Crohn's disease), muscular dystrophy, osteoarthritis, osteoporosis, chronic and/or acute pain (such as neuropathic pain), renal failure, retinal ischemia, septic shock (such as endotoxic shock), and skin aging.

Preferably, the compounds of the invention act as PARP inhibitors to treat or prevent tissue damage resulting from cell death or damage due to necrosis or apoptosis; to treat or prevent neural tissue damage resulting from cerebral ischemia and reperfusion injury or neurodegenerative diseases in an animal; to extend and increase the lifespan and proliferative capacity of cells; to alter gene expression of senescent cells; and to radiosensitize tumor cells.

What the inventors have now discovered is that the ortho-diphenol compounds of the present invention can act to inhibit PART and can ameliorate neural tissue damage and cardiovascular tissue damage, including that following focal ischemia, myocardial infarction, and reperfusion injury. Generally, inhibition of PARP activity spares the cell from energy loss, preventing irreversible depolarization of the neurons and, thus, provides neuroprotection. While not wishing to be bound thereby, it is thought that PARP activation may play a common role in still other excitotoxic mechanisms, perhaps as yet undiscovered, in addition to the production of free radicals and NO. Preferably, the compounds of the invention exhibit an $IC_{50}$ for inhibiting PARP in vitro of about 100 $\mu$M or lower, more preferably, about 25 $\mu$M or lower, most preferably, about 1 $\mu$M or lower.

Preferred PARP inhibitors of the present invention include compounds having formula I:

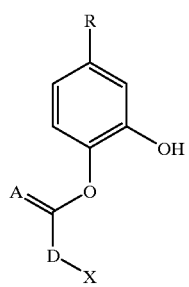

I or a pharmaceutically acceptable salt, hydrate, ester, solvate, prodrug, metabolite, stereoisomer, or mixtures thereof, wherein A is O or S;

R is $C_1$–$C_{10}$ straight or branched chain alkyl, $C_2$–$C_{10}$ straight or branched chain alkenyl, $C_2$–$C_{10}$ straight or branched chain alkynyl, aryl, heteroaryl, carbocycle, or heterocycle;

D is a bond, or a $C_1$–$C_3$ straight or branched chain alkyl, $C_2$–$C_3$ straight or branched chain alkenyl, $C_2$–$C_3$ straight or branched chain alkynyl, wherein any of the carbon atoms of said alkyl, alkenyl, or alkynyl of D are optionally replaced with oxygen, nitrogen, or sulfur; and X is aryl, heteroaryl, carbocycle, or heterocycle;

wherein said alkyl, alkenyl, alkynyl, aryl, heteroaryl, carbocycle, or heterocycle of R, D, or X is optionally substituted with one or more substituents selected from hydroxy, halo, haloalkyl, thiocarbonyl, alkoxy, alkenoxy, alkylaryloxy, aryloxy, arylalkyloxy, cyano, nitro, amino, imino, alkylamino, arylamino, arylazo, arylthio, aminoalkyl, sulfhydryl, thioalkyl, alkylthio, sulfonyl, $C_1$–$C_6$ straight or branched chain alkyl, $C_2$–$C_6$ straight or branched chain alkenyl or alkynyl, aryl, aralkyl, heteroaryl, carbocycle, or heterocycle;

provided that when R is methyl, and D is a bond, then X is not phenyl, 4-nitrophenyl, 4-phenylazo-phenyl, or 3,5-dinitrophenyl; when R is a substituted benzopyran group, and D is a bond, ethenyl, or —NH—, then X is not phenyl, or 3,4,5-trihydroxyphenyl; when R is ethenyl, and D is ethenyl, then X is not 4-hydroxy-3-methoxyphenyl; when R is methyl, and D is ethenyl, then X is not 2-hydroxyphenyl; when R is 1-hydroxy-2-alkylamino-ethyl, and D is a bond, then X is not phenyl, methylphenyl, or 4-methoxyphenyl; and when R is propenyl, and D is a bond, then X is not phenyl.

Preferred compounds of the present invention include compounds of formula I, where R is a hydrophobic group or a $C_1$–$C_{10}$ straight or branched chain alkyl.

Other preferred compounds of the present invention include compounds of formula I, where X is an aryl group; particularly where the aryl group is phenyl. The aryl group may be substituted with at least one non-hydrogen, non-interfering substituent; preferably a halo, hydroxy, amino, nitro, lower alkyl, dimethylamino, acetamide, sulfonyl, aryl, aralkyl, arylthio, —$COOR^1$, —$OR^1$ or —$NHR^1$, where $R^1$ is hydrogen, lower alkyl, or aralkyl substituent.

Still other preferred compounds of the present invention include compounds of formula I where D is a bond.

The following are particularly preferred compounds of the present invention:

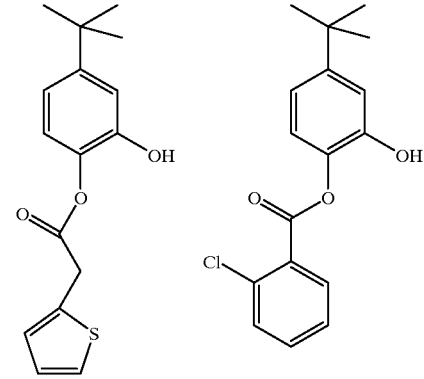

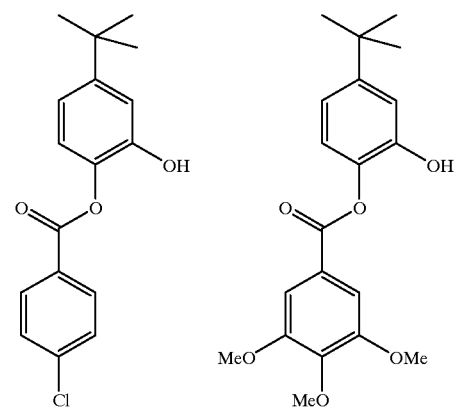

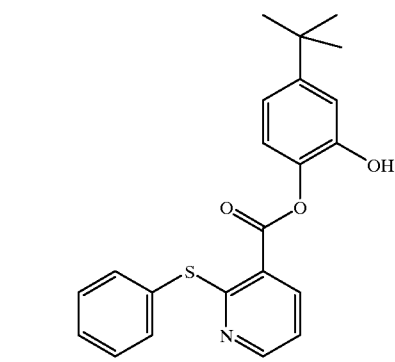

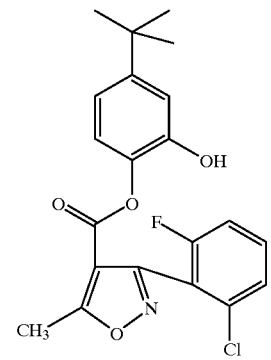

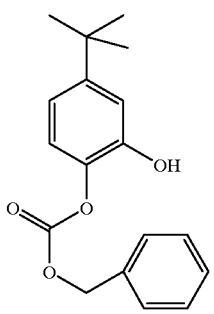

Other preferred compounds of the present invention include compounds 1–51 listed in Table I as follows:

TABLE I

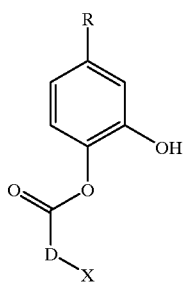

| Compound | R | D | X |
|---|---|---|---|
| 1 | methyl | bond | 4-bromophenyl |
| 2 | ethyl | bond | phenyl |
| 3 | n-propyl | bond | 3,4,5-trihydroxy-phenyl |
| 4 | i-propyl | bond | 3,4,5-trimethoxy-phenyl |
| 5 | n-butyl | bond | 3-hydroxyphenyl |
| 6 | t-butyl | bond | 4-nitro-naphthyl |
| 7 | s-butyl | bond | 3-hydroxy-naphthyl |
| 8 | pentyl | bond | benzyl |
| 9 | hexyl | bond | 4-ethylphenyl |
| 10 | heptyl | bond | 4-ethenylphenyl |
| 11 | octyl | bond | 4-quinolyl |
| 12 | nonyl | bond | 2-thiazolyl |
| 13 | decyl | bond | 3-furyl |
| 14 | 1,1-dimethyl-propyl | bond | phenyl |
| 15 | ethenyl | bond | cyclohexyl |
| 16 | prop-2-enyl | bond | 3-bromocyclohexyl |
| 17 | phenyl | bond | adamantyl |
| 18 | naphthyl | bond | 4-indolyl |
| 19 | 4-nitrophenyl | bond | 2-imidazolyl |
| 20 | 4-hydroxy-phenyl | bond | 1-naphthyl |
| 21 | 4-chlorophenyl | bond | 4-nitrophenyl |
| 22 | 4-methylphenyl | bond | 4-hydroxyphenyl |
| 23 | 4-methoxy-phenyl | bond | 3-piperidyl |
| 24 | 4-dimethyl-amino-phenyl | bond | 3,4,5-trimethyl-phenyl |
| 25 | phenyl-ethyl-phenyl | bond | 3-pyridyl |
| 26 | 4-nitro-3-hydroxy-phenyl | bond | 3,4,5-trifluoro-phenyl |
| 27 | 1-pyridyl | bond | 1-pyrrolidyl |
| 28 | 1-piperidyl | bond | 4-phenylazo-phenyl |
| 29 | 1-pyrrolidyl | 2-bromo-propyl | 4-amino-3-hydroxy-phenyl |
| 30 | cyclohexyl | prop-2-enyl | 3,4,5-triamino-phenyl |
| 31 | cyclopentyl | methyl | 4-hydroxyphenyl |
| 32 | adamantyl | ethyl | phenyl |
| 33 | benzyl | i-propyl | 9-anthracenyl |
| 34 | 4-hydroxy-benzyl | n-propyl | 4-pyrenyl |
| 35 | 3,4,5-trihydroxy-phenyl | 2-imino-propyl | 3-furyl |
| 36 | thiazolyl | 2-thio-propyl | 3-thiophenyl |
| 37 | 2-phenylethyl | 2-sulfonyl-propyl | 4-pyrimidinyl |
| 38 | 3-phenylpropyl | ethenyl | 4-isoquinolyl |
| 39 | 2-phenyl-ethenyl | bond | 4-sulfonylphenyl |
| 40 | 3-phenylprop-2-enyl | chloro-methyl | 4-imino-phenyl |
| 41 | 3-bromopropyl | —$CH_2$—N=CH— | 4-phenylethoxy-phenyl |
| 42 | 4-fluoro-n-butyl | —$CH_2$—S—$CH_2$— | 4-ethylphenoxy-phenyl |
| 43 | 3-methoxy-propyl | —$CH_2$—NH—$CH_2$— | 4-phenoxy-phenyl |
| 44 | 2-hydroxyethyl | —$CH_2$—O—$CH_2$— | 3-phenylpropyl-phenyl |
| 45 | tert-butyl | —$CH_2$— | 2-thienyl |
| 46 | tert-butyl | bond | 2-chloro-phenyl |
| 47 | tert-butyl | bond | 4-chloro-phenyl |
| 48 | tert-butyl | bond | 3,4,5-trimethoxy-phenyl |
| 49 | tert-butyl | bond | (2-phenylthio-3-pyridyl) |
| 50 | tert-butyl | bond | (3-(2-fluoro-6-chlorophenyl)-isoxazol-5-yl) |
| 51 | tert-butyl | —O—$CH_2$—, X attaches directly to the $CH_2$ | phenyl |

Still other preferred compounds of the present invention include compounds 52–102 listed in Table II with formula I where A is S as follows:

TABLE II

Structure I (where A is S): a benzene ring with R at the 4-position, OH at the 2-position, and an O-C(=A)-D-X substituent.

| Compound | R | D | X |
|---|---|---|---|
| 52 | methyl | bond | 4-bromophenyl |
| 53 | ethyl | bond | phenyl |
| 54 | n-propyl | bond | 3,4,5-trihydroxy-phenyl |
| 55 | i-propyl | bond | 3,4,5-trimethoxy-phenyl |
| 56 | n-butyl | bond | 3-hydroxyphenyl |
| 57 | t-butyl | bond | 4-nitro-naphthyl |
| 58 | s-butyl | bond | 3-hydroxy-naphthyl |
| 59 | pentyl | bond | benzyl |
| 60 | hexyl | bond | 4-ethylphenyl |
| 61 | heptyl | bond | 4-ethenylphenyl |
| 62 | octyl | bond | 4-quinolyl |
| 63 | nonyl | bond | 2-thiazolyl |
| 64 | decyl | bond | 3-furyl |
| 65 | 1,1-dimethyl-propyl | bond | phenyl |
| 66 | ethenyl | bond | cyclohexyl |
| 67 | prop-2-enyl | bond | 3-bromocyclohexyl |
| 68 | phenyl | bond | adamantyl |
| 69 | naphthyl | bond | 4-indolyl |
| 70 | 4-nitrophenyl | bond | 2-imidazolyl |
| 71 | 4-hydroxy-phenyl | bond | 1-naphthyl |
| 72 | 4-chlorophenyl | bond | 4-nitrophenyl |
| 73 | 4-methylphenyl | bond | 4-hydroxyphenyl |
| 74 | 4-methoxy-phenyl | bond | 3-piperidyl |
| 75 | 4-dimethyl-amino-phenyl | bond | 3,4,5-trimethyl-phenyl |
| 76 | phenyl-ethyl-phenyl | bond | 3-pyridyl |
| 77 | 4-nitro-3-hydroxy-phenyl | bond | 3,4,5-trifluoro-phenyl |
| 78 | 1-pyridyl | bond | 1-pyrrolidyl |
| 79 | 1-piperidyl | bond | 4-phenylazo-phenyl |
| 80 | 1-pyrrolidyl | 2-bromo-propyl | 4-amino-3-hydroxy-phenyl |
| 81 | cyclohexyl | prop-2-enyl | 3,4,5-triamino-phenyl |
| 82 | cyclopentyl | methyl | 4-hydroxyphenyl |
| 83 | adamantyl | ethyl | phenyl |
| 84 | benzyl | i-propyl | 9-anthracenyl |
| 85 | 4-hydroxy-benzyl | n-propyl | 4-pyrenyl |
| 86 | 3,4,5-trihydroxy-phenyl | 2-imino-propyl | 3-furyl |
| 87 | thiazolyl | 2-thio-propyl | 3-thiophenyl |
| 88 | 2-phenylethyl | 2-sulfonyl-propyl | 4-pyrimidinyl |
| 89 | 3-phenylpropyl | ethenyl | 4-isoquinolyl |
| 90 | 2-phenyl-ethenyl | bond | 4-sulfonylphenyl |
| 91 | 3-phenylprop-2-enyl | chloro-methyl | 4-imino-phenyl |
| 92 | 3-bromopropyl | —CH$_2$—N=CH— | 4-phenylethoxy-phenyl |
| 93 | 4-fluoro-n-butyl | —CH$_2$—S—CH$_2$— | 4-ethylphenoxy-phenyl |
| 94 | 3-methoxy-propyl | —CH$_2$—NH—CH$_2$— | 4-phenoxy-phenyl |
| 95 | 2-hydroxyethyl | —CH$_2$—O—CH$_2$— | 3-phenylpropyl-phenyl |
| 96 | tert-butyl | —CH$_2$— | 2-thienyl |
| 97 | tert-butyl | bond | 2-chloro-phenyl |
| 98 | tert-butyl | bond | 4-chloro-phenyl |
| 99 | tert-butyl | bond | 3,4,5-trimethoxy-phenyl |
| 100 | tert-butyl | bond | 3-(phenylthio)pyridin-2-yl |
| 101 | tert-butyl | bond | 3-(2-chloro-6-fluorophenyl)-5-methylisoxazol-4-yl |
| 102 | tert-butyl | —O—CH$_2$—, X attaches directly to the CH$_2$ | phenyl |

Another especially preferred embodiment of the invention is a pharmaceutical composition which comprises (i) a therapeutically effective amount of the compound of formula I; and (ii) a pharmaceutically acceptable carrier.

As used herein, "alkyl" means a branched or unbranched saturated hydrocarbon chain comprising a designated number of carbon atoms. For example, $C_1$–$C_6$ straight or branched alkyl hydrocarbon chain contains 1 to 6 carbon atoms, and includes but is not limited to substituents such as methyl, ethyl, propyl, iso-propyl, butyl, iso-butyl, tert-butyl, n-pentyl, n-hexyl, and the like, unless otherwise indicated.

"Alkenyl" means a branched or unbranched unsaturated hydrocarbon chain comprising a designated number of carbon atoms. For example, $C_2$–$C_6$ straight or branched alkenyl hydrocarbon chain contains 2 to 6 carbon atoms having at least one double bond, and includes but is not limited to substituents such as ethenyl, propenyl, isopropenyl, butenyl, iso-butenyl, tert-butenyl, n-pentenyl, n-hexenyl, and the like, unless otherwise indicated.

"Alkynyl" refers to a hydrocarbon chain containing a carbon-carbon triple bond. For example, alkynyl groups include, but are not limited to 1-butyne, 2-butyne, 2-pentyne, 3-methyl-1-butyne.

"Alkoxy", means the group —OR wherein R is alkyl as herein defined. Preferably, R is a branched or unbranched saturated hydrocarbon chain containing 1 to 6 carbon atoms.

"Cyclo", used herein as a prefix, refers to a structure characterized by a closed ring.

"Halo" means at least one fluoro, chloro, bromo, or iodo moiety, unless otherwise indicated.

"Amino" compounds include amine ($NH_2$) as well as substituted amino groups comprising alkyls of one through six carbons.

"Ar" and "Aryl" as used herein refers to an aryl or heteroaryl moiety which is substituted or unsubstituted, especially a cyclic or fused cyclic ring and includes a mono-, bi-, or tricyclic, alicylcic, carbocyclic or heterocyclic ring, wherein the ring is either unsubstituted or substituted in one or more position(s) with halo, haloalkyl, hydroxyl, nitro, trifluoromethyl, $C_1$–$C_6$ straight or branched chain alkyl, $C_2$–$C_6$ straight or branched chain alkenyl, $C_1$–$C_6$ alkoxy, $C_2$–$C_6$ alkenyloxy, phenoxy, benzyloxy, amino, thiocarbonyl, ester, thioester, cyano, imino, alkylamino, aminoalkyl, sulfhydryl, thioalkyl, and sulfonyl; wherein the individual ring sizes are 5–8 members; wherein the heterocyclic ring contains 1–4 heteroatom(s) selected from the group consisting of O, N, or S; wherein aromatic or tertiary alkyl amines are optionally oxidized to a corresponding N-oxide. Particularly preferred aryl or heteroaryl moieties include but are not limited to phenyl, benzyl, naphthyl, pyrrolyl, pyrrolidinyl, pyridinyl, pyrimidinyl, purinyl, quinolinyl, isoquinolinyl, furyl, tetrahydrofuryl, thiophenyl, imidazolyl, imidazolinyl, triazinyl, morpholinyl, thiomorpholinyl, oxazolyl, isoxazolyl, triazolyl, tetrahydrothienyl, benzopyranyl, benzofuranyl, benzothienyl, indolyl, indolinyl, indolizinyl, cinnolinyl, phthalazinyl, quinazolinyl, quinoxalinyl, pteridinyl, quinuclidinyl, carbazolyl, acridinyl, phenazinyl, phenothiazinyl, phenoxazinyl, benzimidazolyl, benzthiazolyl, anthracenyl, thiazolyl, isothiazolyl, pyrazinyl, piperazinyl, naphthyridinyl, pyrazolyl, pyrazolidinyl, oxadiazolyl, thiadiazolyl, and thienyl.

"Aralkyl" as used herein refers to an aryl group that is joined to a structure by one or more alkyl groups, e.g., benzyl, phenethyl, and the like. Simiarly, "alkylaryl" refers to an alkyl group that is joined to a structure by one or more aryl groups; and "aryloxy" refers to an aryl group that is joined to a structure by an oxygen group. Other similar combined terms may be interpreted using the same formulation, such as: "arylamino" refers to an aryl group that is joined to a structure by an amino group; or "aryalkyloxy" refers to an aryl group that is joined to a structure by an alkyloxy group, where the last named component, oxygen, is directly joined to the structure.

"Carbocycle" as used herein refers to a cyclic carbon ring structure, which may be saturated or unsaturated, and may also be bridged or unbridged. For example, carbocycle moieties include, but are not limited to, cyclohexyl, cyclopentyl, cycloheptyl, cyclooctyl, adamantyl, and bicyclopentyl.

"Phenyl" includes all possible isomeric phenyl radicals, optionally monosubstituted or multi-substituted with substituents selected from the group consisting of amino, trifluoromethyl, $C_1$–$C_6$ straight or branched chain alkyl, $C_2$–$C_6$ straight or branched chain alkenyl, carbonyl, thiocarbonyl, ester, thioester, alkoxy, alkenoxy, cyano, nitro, imino, alkylamino, aminoalkyl, sulfhydryl, thioalkyl, sulfonyl, hydroxy, halo, haloalkyl, $NR_2$ wherein $R_2$ is selected from the group consisting of hydrogen, ($C_1$–$C_6$)-straight or branched chain alkyl, ($C_3$–$C_6$) straight or branched chain alkenyl or alkynyl, and ($C_1$–$C_4$) bridging alkyl wherein said bridging alkyl forms a heterocyclic ring starting with the nitrogen of $NR_1$ and ending with one of the carbon atoms of said alkyl or alkenyl chain, and wherein said heterocyclic ring is optionally fused to an Ar group.

The compounds of the present invention possess one or more asymmetric center(s) and thus can be produced as mixtures (racemic and non-racemic) of stereoisomers, or as individual enantiomers or diastereomers. The individual stereoisomers may be obtained by using an optically active starting material, by resolving a racemic or non-racemic mixture of an intermediate at some appropriate stage of the synthesis, or by resolution of the compound of formula (I). It is understood that the individual stereoisomers as well as mixtures (racemic and non-racemic) of stereoisomers are encompassed by the scope of the present invention. The S-stereoisomer at atom 1 of formula I is most preferred due to its greater activity.

"Isomers" are different compounds that have the same molecular formula and includes cyclic isomers such as (iso)indole and other isomeric forms of cyclic moieties. "Stereoisomers" are isomers that differ only in the way the atoms are arranged in space. "Enantiomers" are a pair of stereoisomers that are non-superimposable mirror images of each other. "Diastereoisomers" are stereoisomers which are not mirror images of each other. "Racemic mixture" means a mixture containing equal parts of individual enantiomers. "Non-racemic mixture" is a mixture containing unequal parts of individual enantiomers or stereoisomers.

The compounds of the invention may be useful in a free base form, in the form of pharmaceutically acceptable salts, pharmaceutically acceptable hydrates, pharmaceutically acceptable esters, pharmaceutically acceptable solvates, pharmaceutically acceptable prodrugs, pharmaceutically acceptable metabolites, and in the form of pharmaceutically acceptable stereoisomers. These forms are all within the scope of the invention. In practice, the use of these forms amounts to use of the neutral compound.

"Pharmaceutically acceptable salt", "hydrate", "ester" or "solvate" refers to a salt, hydrate, ester, or solvate of the inventive compounds which possesses the desired pharmacological activity and which is neither biologically nor otherwise undesirable. Organic acids can be used to produce salts, hydrates, esters, or solvates such as acetate, adipate, alginate, aspartate, benzoate, benzenesulfonate, p-toluenesulfonate, bisulfate, sulfamate, sulfate, naphthylate, butyrate, citrate, camphorate, camphorsulfonate, cyclopentane-propionate, digluconate, dodecylsulfate, ethanesulfonate, fumarate, glucoheptanoate, glycerophosphate, hemisulfate heptanoate, hexanoate, 2-hydroxyethanesulfonate, lactate, maleate, methanesulfonate, 2-naphthalenesulfonate, nicotinate, oxalate, tosylate and undecanoate. Inorganic acids can be used to produce salts, hydrates, esters, or solvates such as hydrochloride, hydrobromide, hydroiodide, and thiocyanate.

Examples of suitable base salts, hydrates, esters, or solvates include hydroxides, carbonates, and bicarbonates of ammonia, alkali metal salts such as sodium, lithium and potassium salts, alkaline earth metal salts such as calcium and magnesium salts, aluminum salts, and zinc salts.

Salts, hydrates, esters, or solvates may also be formed with organic bases. Organic bases suitable for the formation of pharmaceutically acceptable base addition salts, hydrates, esters, or solvates of the compounds of the present invention include those that are non-toxic and strong enough to form such salts, hydrates, esters, or solvates. For purposes of illustration, the class of such organic bases may include mono-, di-, and trialkylamines, such as methylamine, dimethylamine, triethylamine and dicyclohexylamine; mono-, di- or trihydroxyalkylamines, such as mono-, di-, and triethanolamine; amino acids, such as arginine and lysine; guanidine; N-methyl-glucosamine; N-methyl-glucamine; L-glutamine; N-methyl-piperazine; morpholine; ethylenediamine; N-benzyl-phenethylamine; (trihydroxymethyl)aminoethane; and the like. See, for example, "Pharmaceutical Salts," *J. Pharm. Sci.*, 66:1, 1–19 (1977). Accordingly, basic nitrogen-containing groups can be quaternized with agents including: lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

The acid addition salts, hydrates, esters, or solvates of the basic compounds may be prepared either by dissolving the free base of a PARP inhibitor in an aqueous or an aqueous alcohol solution or other suitable solvent containing the appropriate acid or base, and isolating the salt by evaporating the solution. Alternatively, the free base of the PARP inhibitor may be reacted with an acid, as well as reacting the PARP inhibitor having an acid group thereon with a base, such that the reactions are in an organic solvent, in which case the salt separates directly or can be obtained by concentrating the solution.

"Pharmaceutically acceptable prodrug" refers to a derivative of the inventive compounds which undergoes biotransformation prior to exhibiting its pharmacological effect(s). The prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compounds using methods known in the art, such as those described by *Burger's Medicinal Chemistry and Drug Chemistry*, Fifth Ed., Vol. 1, pp. 172–178, 949–982 (1995). For example, the inventive compounds can be transformed into prodrugs by converting one or more of the hydroxy or carboxy groups into esters.

"Pharmaceutically acceptable metabolite" refers to drugs that have undergone a metabolic transformation. After entry into the body, most drugs are substrates for chemical reactions that may change their physical properties and biologic effects. These metabolic conversions, which usually affect the polarity of the compound, alter the way in which drugs are distributed in and excreted from the body. However, in some cases, metabolism of a drug is required for therapeutic effect. For example, anticancer drugs of the antimetabolite class must be converted to their active forms after they have been transported into a cancer cell. Since must drugs undergo metabolic transformation of some kind, the biochemical reactions that play a role in drug metabolism may be numerous and diverse. The main site of drug metabolism is the liver, although other tissues may also participate.

A feature characteristic of many of these transformations is that the metabolic products are more polar than the parent drugs, although a polar drug does sometimes yield a less polar product. Substances with high lipid/water partition coefficients, which pass easily across membranes, also diffuse back readily from tubular urine through the renal tubular cells into the plasma. Thus, such substances tend to have a low renal clearance and a long persistence in the body. If a drug is metabolized to a more polar compound, one with a lower partition coefficient, its tubular reabsorption will be greatly reduced. Moreover, the specific secretory mechanisms for anions and cations in the proximal renal tubules and in the parenchymal liver cells operate upon highly polar substances.

As a specific example, phenacetin (acetophenetidin) and acetanilide are both mild analgesic and antipyretic agents, but are each transformed within the body to a more polar and more effective metabolite, p-hydroxyacetanilid (acetaminophen), which is widely used today. When a dose of acetanilid is given to a person, the successive metabolites peak and decay in the plasma sequentially. During the first hour, acetanilid is the principal plasma component. In the second hour, as the acetanilid level falls, the metabolite acetaminophen concentration reaches a peak. Finally, after a few hours, the principal plasma component is a further metabolite that is inert and can be excreted from the body. Thus, the plasma concentrations of one or more metabolites, as well as the drug itself, can be pharmacologically important.

The reactions involved in drug metabolism are often classified into two groups, as shown in the Table II. Phase I (or functionalization) reactions generally consist of (1) oxidative and reductive reactions that alter and create new functional groups and (2) hydrolytic reactions that cleave esters and amides to release masked functional groups. These changes are usually in the direction of increased polarity.

Phase II reactions are conjugation reactions in which the drug, or often a metabolite of the drug, is coupled to an endogenous substrate, such as glucuronic acid, acetic acid, or sulfuric acid.

TABLE II

| | Phase I Reactions (functionalization reactions): |
|---|---|
| (1) | Oxidation via the hepatic microsomal P450 system: |
| | Aliphatic oxidation |
| | Aromatic hydroxylation |
| | N-Dealkylation |
| | O-Dealkylation |
| | S-Dealkylation |
| | Epoxidation |
| | Oxidative deamination |
| | Sulfoxide formation |
| | Desulfuration |
| | N-Oxidation and N-hydroxylation |
| | Dehalogenation |
| (2) | Oxidation via nonmicrosomal mechanisms: |
| | Alcohol and aldehyde oxidation |
| | Purine oxidation |
| | Oxidative deamination (monoamine oxidase and diamine oxidase) |
| (3) | Reduction: |
| | Azo and nitro reduction |
| (4) | Hydrolysis: |
| | Ester and amide hydrolysis |
| | Peptide bond hydrolysis |
| | Epoxide hydration |
| | Phase II Reactions (conjugation reactions): |
| (1) | Glucuronidation |
| (2) | Acetylation |
| (3) | Mercapturic acid formation |
| (4) | Sulfate conjugation |

TABLE II-continued

| | |
|---|---|
| (5) | N-, O-, and S-methylation |
| (6) | Trans-sulfuration |

The compounds of the present invention exhibit pharmacological activity and are, therefore, useful as pharmaceuticals. In particular, the compounds exhibit central nervous and cardiac vesicular system activity.

It is understood that tautomeric forms, when possible, are included in the invention. For example, the tautomeric forms of the following compounds are exemplary:

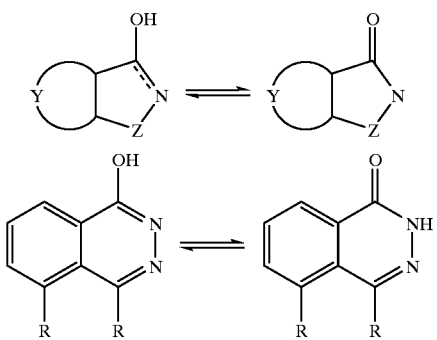

Typically, the novel compounds of the invention will have an IC$_{50}$ for inhibiting poly(ADP-ribose) synthetase in vitro of 100 μM or lower, preferably 50 μM or lower, more preferably 30 μM or lower, more preferably 10 μM or lower, and most preferably 40 nM or lower.

There are multiple routes which may be undertaken to prepare the ortho-diphenol compounds of the present invention using commercially available materials and reagents. An example of one such scheme is set forth below in Scheme I:

SCHEME I

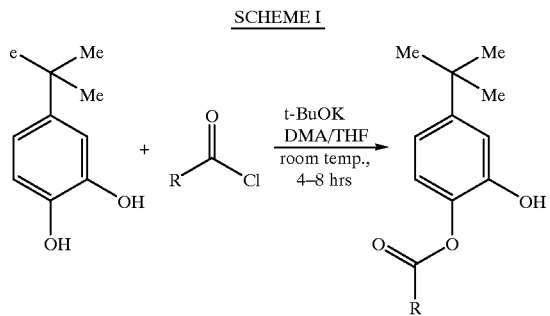

where R is any substituent as described herein, including:

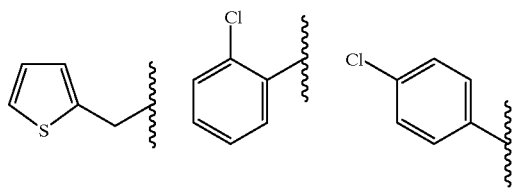

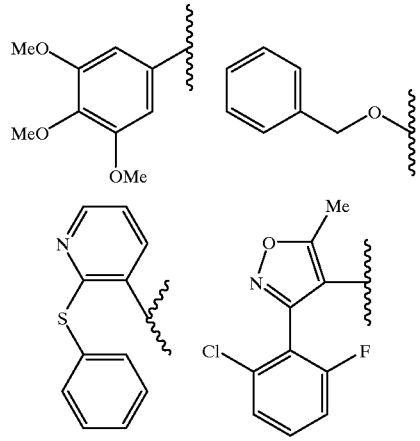

The compounds of the present invention may be synthesized using the synthetic scheme shown in Scheme 1. The starting materials and reagents required for the scheme 1 synthesis of the compounds of the present invention may be obtained from one or more of the following Chemical Supply Companies: Acros, Aldrich, Fluka, JT-Baker, Maybridge, ICN, Lancaster, Sigma, Avocado, Coalite, E-Merck, Eastern-Chemical, EM-Science, Kanto, Octel, and others. To a solution of 4-tert-butylpyrocatechol (1.66 g, 0.01 M) in DMA (50 ml) a powdered t-BuOK (1.12 g, 0.01 M) was added in one portion at room temperature under stirring. The formed solution was stirred for 15 minutes, and the corresponding acid chloride (0.011 M) in THF (10 ml) was added dropwise within 20–30 minutes upon continuous stirring at room temperature. The mixture was stirred for an additional 4–8 hours, and the content was poured into stirred ice-water (100 g). After 3 hours of stirring, the formed solid product was filtered and recrystallized from aqueous ethanol; oily products were extracted with ethyl acetate (2×50 ml). Extracts were thoroughly washed with water (5×50 ml), separated, dried over MgSO$_4$ anhydrous, and the solvents were evaporated in vacuum.

Methods of Using the Compounds of the Invention

The ortho-diphenol compounds of the present invention can treat or prevent tissue damage resulting from cell damage or death due to necrosis or apoptosis; can ameliorate neural or cardiovascular tissue damage, including that following focal ischemia, myocardial infarction, and reperfusion injury; can treat various diseases and conditions caused or exacerbated by PARP activity; can extend or increase the lifespan or proliferative capacity of cells; can alter the gene expression of senescent cells; and can radiosensitize cells. Generally, inhibition of PARP activity spares the cells from energy loss, preventing irreversible depolarization of the neurons, and thus, provides neuroprotection. While not being bound to any one particular theory, it is thought that PARP activation may play a common role in still other excitotoxic mechanisms, perhaps as yet undiscovered, in addition to the production of free radicals and NO.

For the foregoing reasons, the present invention further relates to a method of administering a therapeutically effective amount of the above-identified compounds in an amount sufficient to inhibit PARP activity, to treat or prevent tissue damage resulting from cell damage or death due to necrosis or apoptosis, to effect a neuronal activity not mediated by glutamate neurotoxicity, to effect a neuronal activity mediated by glutamate neurotoxicity, to treat neural tissue damage resulting from ischemia and reperfusion injury, neurological disorders and neurodegenerative diseases; to prevent or treat vascular stroke; to treat or prevent cardiovascular disorders; to treat other conditions and/or disorders such as age-related macular degeneration, AIDS and other immune diseases, arthritis, atherosclerosis, cachexia, cancer, degenerative diseases of skeletal muscle involving replicative senescence, diabetes, head trauma, immune senescence, inflammatory bowel disorders (such as colitis and Crohn's disease), muscular dystrophy, osteoarthritis, osteoporosis, chronic and/or acute pain (such as neuropathic pain), renal failure, retinal ischemia, septic shock (such as endotoxic shock), and skin aging; to extend the lifespan and proliferative capacity of cells; to alter gene expression of senescent cells; or to radiosensitize hypoxic tumor cells. The present invention also relates to treating diseases and conditions in an animal which comprises administering to said animal a therapeutically effective amount of the above-identified compounds.

In particular, the present invention relates to a method of treating, preventing or inhibiting a neurological disorder in an animal, which comprises administering to said animal a therapeutically effective amount of the above-identified compounds. In a particularly preferred embodiment, the neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration. Another preferred embodiment is when the reperfusion injury is a vascular stroke. Yet another preferred embodiment is when the peripheral neuropathy is caused by Guillain-Barre syndrome. Still another preferred embodiment is when the demyelinating disease is multiple sclerosis. Another preferred embodiment is when the neurological disorder relating to neurodegeneration is selected from the group consisting of Alzheimer's Disease, Parkinson's Disease, and amyotrophic lateral sclerosis.

Yet another preferred embodiment is a method of treating, preventing or inhibiting a cardiovascular disease in an animal, such as angina pectoris, myocardial infarction, cardiovascular ischemia, and cardiovascular tissue damage related to PARP activation, by administering to said animal an effective amount of the compounds of the present invention.

The present invention also contemplates the use of compound of Formula I for inhibiting PARP activity; and/or for treating, preventing or inhibiting tissue damage resulting from cell damage or death due to necrosis or apoptosis; and/or for treating, preventing or inhibiting a neurological disorder in an animal.

In a particularly preferred embodiment, the neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration.

Another preferred embodiment is when the reperfusion injury is a vascular stroke. Yet another preferred embodiment is when the peripheral neuropathy is caused by Guillain-Barre syndrome. Still another preferred embodiment is when the demyelinating disease is multiple sclerosis. Another preferred embodiment is when the neurological disorder relating to neurodegeneration is selected from the group consisting of Alzheimer's Disease, Parkinson's Disease, and amyotrophic lateral sclerosis.

The present invention also contemplates the use of the compound of formula I in the preparation of a medicament for the treatment of any of the diseases and disorders in an animal described herein.

In a particular embodiment, the disease or disorder is a neurological disorder.

In a particularly preferred embodiment, the neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration. Another preferred embodiment is when the reperfusion injury is a vascular stroke. Yet another preferred embodiment is when the peripheral neuropathy is caused by Guillain-Barre syndrome.

Still another preferred embodiment is when the demyelinating disease is multiple sclerosis. Another preferred embodiment is when the neurological disorder relating to neurodegeneration is selected from the group consisting of Alzheimer's Disease, Parkinson's Disease, and amyotrophic lateral sclerosis.

The term "preventing neurodegeneration" includes the ability to prevent neurodegeneration in patients newly diagnosed as having a neurodegenerative disease, or at risk of developing a new degenerative disease and for preventing further neurodegeneration in patients who are already suffering from or have symptoms of a neurodegenerative disease.

The term "treatment" as used herein covers any treatment of a disease and/or condition in an animal, particularly a human, and includes:

(i) preventing a disease and/or condition from occurring in a subject which may be predisposed to the disease and/or condition but has not yet been diagnosed as having it;

(ii) inhibiting the disease and/or condition, i.e., arresting its development; or (iii) relieving the disease and/or condition, i.e., causing regression of the disease and/or condition.

As used herein, the term "neural tissue damage resulting from ischemia and reperfusion injury" includes neurotoxicity, such as seen in vascular stroke and global and focal ischemia. As used herein, the term "neurodegenerative diseases," includes Alzheimer's disease, Parkinson's disease and Huntington's disease.

The term "ischemia" relates to localized tissue anemia due to obstruction of the inflow of arterial blood. Global ischemia occurs under conditions in which blood flow to the entire brain ceases for a period of time, such as may result from cardiac arrest. Focal ischemia occurs under conditions in which a portion of the brain is deprived of its normal blood supply, such as may result from thromboembolytic occlusion of a cerebral vessel, traumatic head injury, edema, and brain tumors.

The term "cardiovascular disease" relates to myocardial infarction, angina pectoris, vascular or myocardial ischemia, and related conditions as would be known by those of skill in the art which involve dysfunction of or tissue damage to the heart or vasculature, and especially, but not limited to, tissue damage related to PARP activation.

The term "radiosensitizer", as used herein, is defined as a molecule, preferably a low molecular weight molecule, administered to animals in therapeutically effective amounts to increase the sensitivity of the cells to be radiosensitized to electromagnetic radiation and/or to promote the treatment of diseases which are treatable with electromagnetic radiation. Diseases which are treatable with electromagnetic radiation include neoplastic diseases, benign and malignant tumors, and cancerous cells. Electromagnetic radiation treatment of other diseases not listed herein are also contemplated by the present invention. The terms "electromagnetic radiation" and "radiation" as used herein includes, but is not limited to, radiation having the wavelength of $10^{-20}$ to $10^0$ meters. Preferred embodiments of the present invention employ the electromagnetic radiation of: gamma-radiation ($10^{-20}$ to $10^{-13}$ m) x-ray radiation ($10^{-11}$ to $10^{-9}$ m), ultraviolet light (10 nm to 400 nm), visible light (400 nm to 700 nm), infrared radiation (700 nm to 1.0 mm), and microwave radiation (1 mm to 30 cm).

Compositions and Methods for Effecting Neuronal Activity

Preferably, the compounds of the invention inhibit PARP activity and, thus, are believed to be useful for treating neural tissue damage, particularly damage resulting from cerebral ischemia and reperfusion injury or neurodegenerative diseases in animals. The term "nervous tissue" refers to the various components that make up the nervous system including, without limitation, neurons, neural support cells, glia, Schwann cells, vasculature contained within and supplying these structures, the central nervous system, the brain, the brain stem, the spinal cord, the junction of the central nervous system with the peripheral nervous system, the peripheral nervous system, and allied structures.

Further, according to the invention, an effective therapeutic amount of the compounds and compositions described above are administered to animals to effect a neuronal activity, particularly one that is not mediated by NMDA-receptor mediated neurotoxicity. Such neuronal activity may consist of stimulation of damaged neurons, promotion of neuronal regeneration, prevention of neurodegeneration and treatment of a neurological disorder. Accordingly, the present invention further relates to a method of effecting a neuronal activity in an animal, comprising administering an effective amount of the compound of formula I to said animal.

Examples of neurological disorders that are treatable by the method of using the present invention include, without limitation, trigeminal neuralgia; glossopharyngeal neuralgia; Bell's Palsy; myasthenia gravis; muscular dystrophy; amyotrophic lateral sclerosis; progressive muscular atrophy; progressive bulbar inherited muscular atrophy; herniated, ruptured or prolapsed invertebrate disk syndromes; cervical spondylosis; plexus disorders; thoracic outlet destruction syndromes; peripheral neuropathies such as those caused by lead, dapsone, ticks, porphyria, or Guillain-Barré syndrome; Alzheimer's disease; Huntington's Disease and Parkinson's disease. The term "neurodegenerative diseases" includes Alzheimer's disease, Parkinson's disease and Huntington's disease.

The term "nervous insult" refers to any damage to nervous tissue and any disability or death resulting therefrom. The cause of nervous insult may be metabolic, toxic, neurotoxic, iatrogenic, thermal or chemical, and includes without limitation, ischemia, hypoxia, cerebrovascular accident, trauma, surgery, pressure, mass effect, hemmorrhage, radiation, vasospasm, neurodegenerative disease, infection, Parkinson's disease, amyotrophic lateral sclerosis (ALS), myelination/demyelination process, epilepsy, cognitive disorder, glutamate abnormality and secondary effects thereof.

The term "neuroprotective" refers to the effect of reducing, arresting or ameliorating nervous insult, and protecting, resuscitating, or reviving nervous tissue that has suffered nervous insult.

The term "preventing neurodegeneration" includes the ability to prevent neurodegeneration in patients diagnosed as having a neurodegenerative disease or who are at risk of developing a neurodegenerative disease. The term also encompasses preventing further neurodegeneration in patients who are already suffering from or have symptoms of a neurodegenerative disease.

The term "treating" refers to:
(i) preventing a disease, disorder or condition from occurring in an animal that may be predisposed to the disease, disorder and/or condition, but has not yet been diagnosed as having it;
(ii) inhibiting the disease, disorder or condition, i.e., arresting its development; and
(iii) relieving the disease, disorder or condition, i.e., causing regression of the disease, disorder and/or condition.

The method of the present invention is particularly useful for treating a neurological disorder selected from the group consisting of: peripheral neuropathy caused by physical injury or disease state; head trauma, such as traumatic brain injury; physical damage to the spinal cord; stroke associated with brain damage, such as vascular stroke associated with hypoxia and brain damage, focal cerebral ischemia, global cerebral ischemia, and cerebral reperfusion injury; demyelinating diseases, such as multiple sclerosis; and neurological disorders related to neurodegeneration, such as Alzheimer's Disease, Parkinson's Disease, Huntington's Disease and amyotrophic lateral sclerosis (ALS).

The term "neural tissue damage resulting from ischemia and reperfusion injury and neurodegenerative diseases" includes neurotoxicity, such as seen in vascular stroke and global and focal ischemia.

Treating Other PARP-Related Disorders

The compounds, compositions and methods of the present invention are particularly useful for treating or preventing tissue damage resulting from cell death or damage due to necrosis or apoptosis.

The compounds, compositions and methods of the invention can also be used to treat a cardiovascular disorder in an animal, by administering an effective amount of the compound of formula to the animal. As used herein, the term "cardiovascular disorders" refers to those disorders that can either cause ischemia or are caused by reperfusion of the heart. Examples include, but are not limited to, coronary artery disease, angina pectoris, myocardial infarction, cardiovascular tissue damage caused by cardiac arrest, cardiovascular tissue damage caused by cardiac bypass, cardiogenic shock, and related conditions that would be known by those of ordinary skill in the art or which involve dysfunction of or tissue damage to the heart or vasculature, especially, but not limited to, tissue damage related to PARP activation.

For example, the methods of the invention are believed to be useful for treating cardiac tissue damage, particularly damage resulting from cardiac ischemia or caused by reperfusion injury in animals. The methods of the invention are particularly useful for treating cardiovascular disorders selected from the group consisting of: coronary artery disease, such as atherosclerosis; angina pectoris; myocardial infarction; myocardial ischemia and cardiac arrest; cardiac bypass; and cardiogenic shock. The methods of the invention are particularly helpful in treating the acute forms of the above cardiovascular disorders.

Further, the methods of the invention can be used to treat tissue damage resulting from cell damage or death due to necrosis or apoptosis, neural tissue damage resulting from ischemia and reperfusion injury, neurological disorders and neurodegenerative diseases; to prevent or treat vascular stroke; to treat or prevent cardiovascular disorders; to treat other conditions and/or disorders such as age-related macular degeneration, AIDS and other immune diseases, arthritis, atherosclerosis, cachexia, cancer, degenerative diseases of skeletal muscle involving replicative senescence, diabetes, head trauma, immune senescence, inflammatory bowel disorders (such as colitis and Crohn's disease), muscular dystrophy, osteoarthritis, osteoporosis, chronic and/or acute pain (such as neuropathic pain), renal failure, retinal ischemia, septic shock (such as endotoxic shock), and skin aging; to extend the lifespan and proliferative capacity of cells; to alter gene expression of senescent cells; or to radiosensitize tumor cells.

Further still, the methods of the invention can be used to treat cancer and to radiosensitize tumor cells. The term "cancer" is interpreted broadly. The compounds of the present invention can be "anti-cancer agents", which term also encompasses "anti-tumor cell growth agents" and "anti-neoplastic agents". For example, the methods of the invention are useful for treating cancers and radiosensitizing tumor cells in cancers such as ACTH-producing tumors, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovarian cancer, ovary (germ cell) cancer, prostate cancer, pancreatic cancer, penile cancer, retinoblastoma, skin cancer, soft-tissue sarcoma, squamous cell carcinomas, stomach cancer, testicular cancer, thyroid cancer, trophoblastic neoplasms, uterine cancer, vaginal cancer, cancer of the vulva and Wilm's tumor.

The term "radiosensitizer", as used herein, is defined as a molecule, preferably a low molecular weight molecule, administered to animals in therapeutically effective amounts to increase the sensitivity of the cells to be radiosensitized to electromagnetic radiation and/or to promote the treatment of diseases which are treatable with electromagnetic radiation. Diseases which are treatable with electromagnetic radiation include neoplastic diseases, benign and malignant tumors, and cancerous cells. Electromagnetic radiation treatment of other diseases not listed herein are also contemplated by the present invention. The terms "electromagnetic radiation" and "radiation" as used herein includes, but is not limited to, radiation having the wavelength of $10^{-20}$ to $10^0$ meters. Preferred embodiments of the present invention employ the electromagnetic radiation of: gamma-radiation ($10^{-20}$ to $10^{-13}$ m) x-ray radiation ($10^{-11}$ to $10^{-9}$ m), ultraviolet light (10 nm to 400 nm), visible light (400 nm to 700 nm), infrared radiation (700 nm to 1.0 mm), and microwave radiation (1 mm to 30 cm).

Radiosensitizers are known to increase the sensitivity of cancerous cells to the toxic effects of electromagnetic radiation. Several mechanisms for the mode of action of radiosensitizers have been suggested in the literature including: hypoxic cell radiosensitizers (e.g., 2-nitro-imidazole compounds, and benzotriazine dioxide compounds) promote the reoxygenation of hypoxic tissue and/or catalyze the generation of damaging oxygen radicals; non-hypoxic cell radiosensitizers (e.g., halogenated pyrimidines) can be analogs of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers activated by the electromagnetic radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, NPe6, tin etioporphyrin SnET2, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumor with or without additional radiation; or other therapeutically effective compounds for treating cancer or other disease. Examples of additional therapeutic agents that may be used in conjunction with radiosensitizers include, but are not limited to: 5-fluorouracil, leucovorin, 5'-amino-5'deoxythymidine, oxygen, carbogen, red cell transfusions, perfluorocarbons (e.g., Fluosol-DA), 2,3-DPG, BW12C, calcium channel blockers, pentoxyfylline, antiangiogenesis compounds, hydralazine, and L-BSO. Examples of chemotherapeutic agents that may be used in conjunction with radiosensitizers include, but are not limited to: adriamycin, camptothecin, carboplatin, cisplatin, daunorubicin, docetaxel, doxorubicin, interferon (alpha, beta, gamma), interleukin 2, irinotecan, paclitaxel, topotecan, and therapeutically effective analogs and derivatives of the same.

The compounds of the present invention may also be used for radiosensitizing tumor cells.

The term "treating" refers to:
(i) preventing a disease, disorder or condition from occurring in an animal that may be predisposed to the disease, disorder and/or condition, but has not yet been diagnosed as having it;
(ii) inhibiting the disease, disorder or condition, i.e., arresting its development; and
(iii) relieving the disease, disorder or condition, i.e., causing regression of the disease, disorder and/or condition.

Pharmaceutical Compositions of the Invention

The present invention also relates to a pharmaceutical composition comprising (i) a therapeutically effective amount of the compound of formula I and (ii) a pharmaceutically acceptable carrier.

The above discussion relating to the preferred embodiments' utility and administration of the compounds of the present invention also applies to the pharmaceutical composition of the present invention.

The term "pharmaceutically acceptable carrier" as used herein refers to any carrier, diluent, excipient, suspending agent, lubricating agent, adjuvant, vehicle, delivery system, emulsifier, disintegrant, absorbent, preservative, surfactant, colorant, flavorant, or sweetener.

For these purposes, the composition of the invention may be administered orally, parenterally, by inhalation spray, topically, rectally, nasally, bucally, vaginally, intraventricularly, via an implanted reservoir in dosage formulations containing conventional non-toxic pharmaceutically-acceptable carriers, or by any other convenient dosage form. The term parenteral as used herein includes subcutaneous, intravenous, intramuscular, intraperitoneal, intrathecal, intraventricular, intrasternal, and intracranial injection or infusion techniques.

When administered parenterally, the composition will normally be in a unit dosage, sterile injectable form (solution, suspension or emulsion) which is preferably isotonic with the blood of the recipient with a pharmaceutically acceptable carrier. Examples of such sterile injectable forms are sterile injectable aqueous or oleaginous suspensions. These suspensions may be formulated according to techniques known in the art using suitable dispersing or wetting agents and suspending agents. The sterile injectable forms may also be sterile injectable solutions or suspensions in non-toxic parenterally-acceptable diluents or solvents, for example, as solutions in 1,3-butanediol. Among the acceptable vehicles and solvents that may be employed are water, saline, Ringer's solution, dextrose solution, isotonic sodium chloride solution, and Hanks' solution. In addition, sterile, fixed oils are conventionally employed as solvents or suspending mediums. For this purpose, any bland fixed oil may be employed including synthetic mono- or di-glycerides, corn, cottonseed, peanut, and sesame oil. Fatty acids such as ethyl oleate, isopropyl myristate, and oleic acid and its glyceride derivatives, including olive oil and castor oil, especially in their polyoxyethylated versions, are useful in the preparation of injectables. These oil solutions or suspensions may also contain long-chain alcohol diluents or dispersants.

Sterile saline is a preferred carrier, and the compounds are often sufficiently water soluble to be made up as a solution for all foreseeable needs. The carrier may contain minor amounts of additives, such as substances that enhance solubility, isotonicity, and chemical stability, e.g., antioxidants, buffers and preservatives.

Formulations suitable for nasal or buccal administration (such as self-propelling powder dispensing formulations) may comprise about 0.1% to about 5% w/w, for example 1% w/w of active ingredient. The formulations for human medical use of the present invention comprise an active ingredient in association with a pharmaceutically acceptable carrier therefore and optionally other therapeutic ingredient(s).

When administered orally, the composition will usually be formulated into unit dosage forms such as tablets, cachets, powder, granules, beads, chewable lozenges, capsules, liquids, aqueous suspensions or solutions, or similar dosage forms, using conventional equipment and techniques known in the art. Such formulations typically include a solid, semisolid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, and the like.

The composition of the invention is preferably administered as a capsule or tablet containing a single or divided dose of the inhibitor. Preferably, the composition is administered as a sterile solution, suspension, or emulsion, in a single or divided dose. Tablets may contain carriers such as lactose and corn starch, and/or lubricating agents such as magnesium stearate. Capsules may contain diluents including lactose and dried corn starch.

A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Molded tablets may be made by molding in a suitable machine, a mixture of the powdered active ingredient and a suitable carrier moistened with an inert liquid diluent.

The compounds of this invention may also be administered rectally in the form of suppositories. These compositions can be prepared by mixing the drug with a suitable non-irritating excipient which is solid at room temperature, but liquid at rectal temperature, and, therefore, will melt in the rectum to release the drug. Such materials include cocoa butter, beeswax, and polyethylene glycols.

Compositions and methods of the invention also may utilize controlled release technology. Thus, for example, the inventive compounds may be incorporated into a hydrophobic polymer matrix for controlled release over a period of days. The composition of the invention may then be molded into a solid implant suitable for providing efficacious concentrations of the PARP inhibitors over a prolonged period of time without the need for frequent re-dosing. Such controlled release films are well known to the art. Particularly preferred are transdermal delivery systems. Other examples of polymers commonly employed for this purpose that may be used in the present invention include nondegradable ethylene-vinyl acetate copolymer an degradable lactic acid-glycolic acid copolymers which may be used externally or internally. Certain hydrogels such as poly (hydroxyethylmethacrylate) or poly(vinylalcohol) also may be useful, but for shorter release cycles than the other polymer release systems, such as those mentioned above.

In a preferred embodiment, the carrier is a solid biodegradable polymer or mixture of biodegradable polymers with appropriate time release characteristics and release kinetics. The composition of the invention may then be molded into a solid implant suitable for providing efficacious concentrations of the compounds of the invention over a prolonged period of time without the need for frequent re-dosing. The composition of the present invention can be incorporated into the biodegradable polymer or polymer mixture in any suitable manner known to one of ordinary skill in the art and may form a homogeneous matrix with the biodegradable polymer, or may be encapsulated in some way within the polymer, or may be molded into a solid implant.

In one embodiment, the biodegradable polymer or polymer mixture is used to form a soft "depot" containing the pharmaceutical composition of the present invention that can be administered as a flowable liquid, for example, by injection, but which remains sufficiently viscous to maintain the pharmaceutical composition within the localized area around the injection site. The degradation time of the depot so formed can be varied from several days to a few years, depending upon the polymer selected and its molecular weight. By using a polymer composition in injectable form, even the need to make an incision may be eliminated. In any event, a flexible or flowable delivery "depot" will adjust to the shape of the space it occupies with the body with a minimum of trauma to surrounding tissues. The pharmaceutical composition of the present invention is used in amounts that are therapeutically effective, and may depend upon the desired release profile, the concentration of the pharmaceutical composition required for the sensitizing effect, and the length of time that the pharmaceutical composition has to be released for treatment.

The PARP inhibitors are used in the composition in amounts that are therapeutically effective. Said compositions may be sterilized and/or contain adjuvants, such as preserving, stabilizing, welling, or emulsifying agents, solution promoters, salts for regulating the osmotic pressure, and/or buffers. In addition, they may also contain other therapeutically valuable substances. Said compositions are prepared according to conventional mixing, granulating, or coating methods, and contain about 0.1 to 75%, preferably about 1 to 50%, of the active ingredient.

To be effective therapeutically as central nervous system targets, the compounds of the present invention should readily penetrate the blood-brain barrier when peripherally administered. Compounds which cannot penetrate the blood-brain barrier can be effectively administered by an intraventricular route or other appropriate delivery system suitable for administration to the brain.

Doses of the compounds preferably include pharmaceutical dosage units comprising an efficacious quantity of active compound. By an efficacious quantity is meant a quantity sufficient to inhibit PARP and derive the beneficial effects therefrom through administration of one or more of the pharmaceutical dosage units. Preferably, the dose is sufficient to prevent or reduce the effects of vascular stroke or other neurodegenerative diseases.

For medical use, the amount required of the active ingredient to achieve a therapeutic effect will vary with the particular compound, the route of administration, the mammal under treatment, and the particular disorder or disease being treated. A suitable systematic dose of a compound of the present invention or a pharmacologically acceptable salt thereof for a mammal suffering from, or likely to suffer from, any of condition as described hereinbefore is in the range of about 0.01 mg/kg to about 100 mg/kg of the active ingredient compound, the most preferred dosage being about 0.1 to about 10 mg/kg.

It is understood, however, that a specific dose level for any particular patient will depend upon a variety of factors including the activity of the specific compound employed, the molecular weight of the specific compound employed, the age, body weight, general health, sex, diet, time of administration, rate of excretion, drug combination, and the severity of the particular disease being treated and form of administration.

It is understood that the ordinarily skilled physician or veterinarian will readily determine and prescribe the effective amount of the compound for prophylactic or therapeutic treatment of the condition for which treatment is administered. In so proceeding, the physician or veterinarian could employ an intravenous bolus followed by an intravenous infusion and repeated administrations, parenterally or orally, as considered appropriate. While it is possible for an active ingredient to be administered alone, it is preferable to present it as a formulation.

When preparing dosage form incorporating the compositions of the invention, the compounds may also be blended with conventional excipients such as binders, including gelatin, pregelatinized starch, and the like; lubricants, such as hydrogenated vegetable oil, stearic acid, and the like; diluents, such as lactose, mannose, and sucrose; disintegrants, such as carboxymethylcellulose and sodium starch glycolate; suspending agents, such as povidone, polyvinyl alcohol, and the like; absorbents, such as silicon dioxide; preservatives, such as methylparaben, propylparaben, and sodium benzoate; surfactants, such as sodium lauryl sulfate, polysorbate 80, and the like; colorants such as F.D.& C. dyes and lakes; flavorants; and sweeteners.

The present invention relates to the use of the compounds of formula I in the preparation of a medicament for the treatment of any disease or disorder in an animal described herein.

PARP Assay

A convenient method to determine $IC_{50}$ of a PARP inhibitor compound is a PARP assay using purified recombinant human PARP from Trevigan (Gaithersburg, Md.), as follows: The PARP enzyme assay is set up on ice in a volume of 100 microliters consisting of 100 mM Tris-HCl (pH 8.0), 1 mM $MgCl_2$, 28 mM KCl, 28 mM NaCl, 0.1 mg/ml of herring sperm DNA (activated as a 1 mg/ml stock for 10 minutes in a 0.15% hydrogen peroxide solution), 3.0 micromolar [3H]nicotinamide adenine dinucleotide (470 mci/mmole), 7 micrograms/ml PARP enzyme, and various concentrations of the compounds to be tested. The reaction is initiated by incubating the mixture at 25° C. After 15 minutes of incubation, the reaction is terminated by adding 500 microliters of ice cold 20% (w/v) trichloroacetic acid. The precipitate formed is transferred onto a glass fiber filter (Packard Unifilter-GF/B) and washed three times with ethanol. After the filter is dried, the radioactivity is determined by scintillation counting. The compounds of this invention were found to have potent enzymatic activity in the range of a few nM to 20 M in $IC_{50}$ in this inhibition assay.

Focal cerebral ischemia experiments were performed using male Wistar rats weighing 250–300 g which were anesthetized with 4% halothane. This anesthesia was maintained with 1.0–1.5% halothane until the end of the surgery. The animals were placed in a warm environment to avoid a decrease of body temperature during surgery. An anterior midline cervical incision was made. The right common carotid artery (CCA) was exposed and was isolated from the vagus nerve. A silk suture was placed and tied around the CCA in proximity to the heart. The external carotid artery (ECA) was then exposed and was ligated with a silk suture. A puncture was made in the CCA and a small catheter (PE 10, Ulrich & Co., St-Gallen, Switzerland) was gently advanced to the lumen of the internal carotid artery (ICA). The pterygopalatine artery was not occluded. The catheter was tied in place with a silk suture. Then, a 4-0 nylon suture (Braun Medical, Crissier, Switzerland) was introduced into the catheter lumen and was pushed until the tip blocked the anterior cerebral artery. The length of catheter advanced into the ICA was approximately 19 mm from the origin of the ECA. The suture was maintained in this position by occlusion of the catheter by heat. One cm of catheter and nylon suture were left protruding so that the suture could be withdrawn to allow reperfusion. The skin incision was then closed with wound clips and the animals maintained in a warm environment during recovery from anesthesia. Two hours later, the animals were re-anesthized, the clips were discarded and the wound re-opened. The catheter was cut and the suture was pulled out. The catheter was then obturated again by heat, and wound clips were placed on the wound. The animals were allowed to survive for 24 hours with free access to food and water. The rats were sacrificed with $CO_2$ and were decapitated. The brains were immediately removed, frozen on dry ice and stored at −80° C. The brains were then cut in 0.02 mm-thick sections in a cryocut at −19° C., taking one of every 20 sections. The sections were stained with cresyl violet according to the Nissl procedure. Each section was examined under a light microscope and the regional infarct area was determined according to the presence of cells with morphological changes. Various doses of compounds were tested in this model. The compounds were given in either single or multiple doses, i.p. or i.v., at different times before or after the onset of ischemia. Compounds of this invention were found to have protection in the range of 20 to 80 percent in this assay.

The experiments of the heart ischemia/reperfusion injury model were performed using female Sprague-Dawley rats weighing 300–350 g which were anesthetized with intraperitoneal ketamine at a dose of 150 mg/kg. The rats were endotracheally incubated and ventilated with oxygen-enriched room air using a Harvard rodent ventilator. Polyethylene catheters inserted into the carotid artery and the femoral vein were used for artery blood pressure monitoring and fluid administration, respectively. Arterial $pCO_2$ was maintained between 35 and 45 mm Hg by adjusting the respiratory rate. The rat chests were opened by median sternotomy, the pericardium was incised, and the hearts were cradled with a latex membrane tent. Hemodynamic data were obtained at baseline after at least 15 minute stabilization from the end of the surgical operation. The LAD (left anterior descending) coronary artery was ligated for 40 minutes and was followed by 120 minutes of reperfusion. After 120 minutes of reperfusion, the LAD artery was reoccluded, and a 0.1 ml bolus of monastral blue dye was injected into the left atrium to determine the ischemic risk region. The hearts were then arrested with potassium chloride. The hearts were cut into five 2–3 mm thick transverse slices, and each slice was weighed. The sections were incubated in a 1% solution of triphenyltetrazolium chloride to visualize the infarcted myocardium located within the risk region. Infarct size was calculated by summing the values for each left ventricular slice and expressed as a fraction of the risk region of the left ventricle. Various doses of compounds were tested in this model. The compounds were given in either single or multiple doses, i.p or i.v., at different times before or after the onset of ischemia. The compounds of this invention were found to have ischemia/reperfusion injury protection in the range of 10 to 40 percent in this assay.

As a result of their demonstrated PARP inhibition, the compounds of this invention protect against ischemia-induced degeneration of rat hippocampal neurons in vitro and thus may be useful in disorders arising from cerebral ischemia such as stroke, septic shock, or CNS degenerative disorders. They may also be useful in protecting the spinal cord following trauma. As an experimental result of ischemia/reperfusion injury in rats, the present invention is further directed to a method of prophylactic or therapeutic treatment of heart attack, cardiac arrest, cardiac bypass, diabetes, or risk of damage which comprises administering an effective amount of a compound of the present invention for PARP inhibition in unit dosage form.

EXAMPLES

Further understanding of the present invention may be made by reference to the following examples:

Example 1

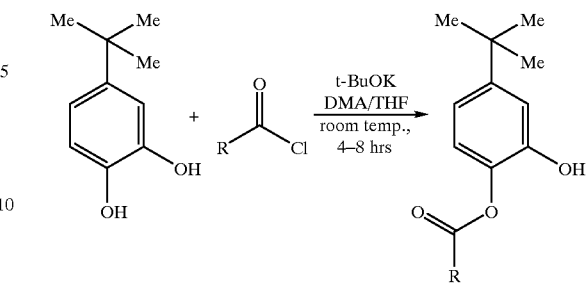

where R is any substituent as described herein, including:

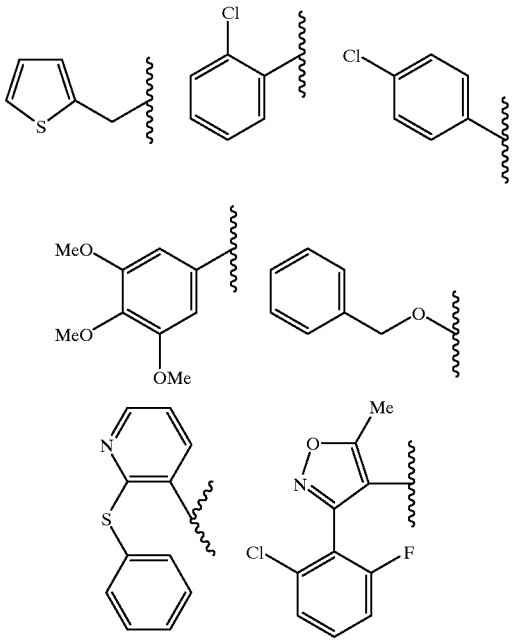

The compounds of the present invention may be synthesized using the synthetic scheme shown in Example 1. The starting materials and reagents required for the synthesis of the compounds of the present invention may be obtained from one or more of the following Chemical Supply Companies: Acros, Aldrich, Fluka, JT-Baker, Maybridge, ICN, Lancaster, Sigma, Avocado, Coalite, E-Merck, Eastern-Chemical, EM-Science, Kanto, Octel, and others. To a solution of 4-tert-butylpyrocatechol (1.66 g, 0.01 M) in DMA (50 ml) a powdered t-BuOK (1.12 g, 0.01 M) was added in one portion at room temperature under stirring. The formed solution was stirred for 15 minutes, and the corresponding acid chloride (0.011 M) in THF (10 ml) was added dropwise within 20–30 minutes upon continuous stirring at room temperature. The mixture was stirred for an additional 4–8 hours, and the content was poured into stirred ice-water (100 g). After 3 hours of stirring, the formed solid product was filtered and recrystallized from aqueous ethanol; oily products were extracted with ethyl acetate (2×50 ml). Extracts were thoroughly washed with water (5×50 ml), separated, dried over $MgSO_4$ anhydrous, and the solvents were evaporated in vacuum.

Example 2

Preparation of Other Ortho-Diphenol Compounds

Using the synthesis schemes described above and the methods of the preceding examples, the following compounds of formula I are synthesized:

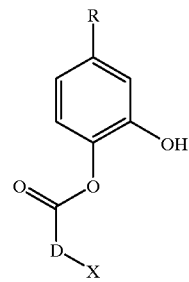

| Compound | R | D | X |
|---|---|---|---|
| 1 | methyl | bond | 4-bromophenyl |
| 2 | ethyl | bond | phenyl |
| 3 | n-propyl | bond | 3,4,5-trihydroxyphenyl |
| 4 | i-propyl | bond | 3,4,5-trimethoxyphenyl |
| 5 | n-butyl | bond | 3-hydroxyphenyl |
| 6 | t-butyl | bond | 4-nitro-naphthyl |
| 7 | s-butyl | bond | 3-hydroxy-naphthyl |
| 8 | pentyl | bond | benzyl |
| 9 | hexyl | bond | 4-ethylphenyl |
| 10 | heptyl | bond | 4-ethenylphenyl |
| 11 | octyl | bond | 4-quinolyl |
| 12 | nonyl | bond | 2-thiazolyl |
| 13 | decyl | bond | 3-furyl |
| 14 | 1,1-dimethyl-propyl | bond | phenyl |
| 15 | ethenyl | bond | cyclohexyl |
| 16 | prop-2-enyl | bond | 3-bromocyclohexyl |
| 17 | phenyl | bond | adamantyl |
| 18 | naphthyl | bond | 4-indolyl |
| 19 | 4-nitrophenyl | bond | 2-imidazolyl |
| 20 | 4-hydroxyphenyl | bond | 1-naphthyl |
| 21 | 4-chlorophenyl | bond | 4-nitrophenyl |
| 22 | 4-methylphenyl | bond | 4-hydroxyphenyl |
| 23 | 4-methoxyphenyl | bond | 3-piperidyl |
| 24 | 4-dimethylamino-phenyl | bond | 3,4,5-trimethylphenyl |
| 25 | phenyl-ethyl-phenyl | bond | 3-pyridyl |
| 26 | 4-nitro-3-hydroxy-phenyl | bond | 3,4,5-trifluorophenyl |
| 27 | 1-pyridyl | bond | 1-pyrrolidyl |
| 28 | 1-piperidyl | bond | 4-phenylazo-phenyl |
| 29 | 1-pyrrolidyl | 2-bromo-propyl | 4-amino-3-hydroxy-phenyl |
| 30 | cyclohexyl | prop-2-enyl | 3,4,5-triamino-phenyl |
| 31 | cyclopentyl | methyl | 4-hydroxyphenyl |
| 32 | adamantyl | ethyl | phenyl |
| 33 | benzyl | i-propyl | 9-anthracenyl |
| 34 | 4-hydroxy-benzyl | n-propyl | 4-pyrenyl |
| 35 | 3,4,5-trihydroxy-phenyl | 2-imino-propyl | 3-furyl |
| 36 | thiazolyl | 2-thio-propyl | 3-thiophenyl |
| 37 | 2-phenylethyl | 2-sulfonyl-propyl | 4-pyrimidinyl |

-continued

| Compound | R | D | X |
|---|---|---|---|
| 38 | 3-phenylpropyl | ethenyl | 4-isoquinolyl |
| 39 | 2-phenyl-ethenyl | bond | 4-sulfonylphenyl |
| 40 | 3-phenylprop-2-enyl | chloro-methyl | 4-imino-phenyl |
| 41 | 3-bromopropyl | —$CH_2$—N=CH— | 4-phenylethoxy-phenyl |
| 42 | 4-fluoro-n-butyl | —$CH_2$—S—$CH_2$— | 4-ethylphenoxy-phenyl |
| 43 | 3-methoxy-propyl | —$CH_2$—NH—$CH_2$— | 4-phenoxy-phenyl |
| 44 | 2-hydroxyethyl | —$CH_2$—O—$CH_2$— | 3-phenylpropyl-phenyl |
| 45 | tert-butyl | —$CH_2$— | (2-thienyl) |
| 46 | tert-butyl | bond | 2-chloro-phenyl |
| 47 | tert-butyl | bond | 4-chloro-phenyl |
| 48 | tert-butyl | bond | 3,4,5-trimethoxy-phenyl |
| 49 | tert-butyl | bond | (phenylthio-pyridyl) |
| 50 | tert-butyl | bond | (fluoro-chloro-phenyl-methylisoxazolyl) |
| 51 | tert-butyl | —O—$CH_2$—, X attaches directly to the $CH_2$ | phenyl |

Example 3

Preparation of Other Ortho-Diphenol Compounds

Using the synthesis schemes described above and the methods of the preceding examples, the following compounds of formula I where A is S are synthesized:

where A is S

| Compound | R | D | X |
|---|---|---|---|
| 52 | methyl | bond | 4-bromophenyl |
| 53 | ethyl | bond | phenyl |
| 54 | n-propyl | bond | 3,4,5-trihydroxy-phenyl |
| 55 | i-propyl | bond | 3,4,5-trimethoxy-phenyl |
| 56 | n-butyl | bond | 3-hydroxyphenyl |
| 57 | t-butyl | bond | 4-nitro-naphthyl |
| 58 | s-butyl | bond | 3-hydroxy-naphthyl |
| 59 | pentyl | bond | benzyl |
| 60 | hexyl | bond | 4-ethylphenyl |
| 61 | heptyl | bond | 4-ethenylphenyl |
| 62 | octyl | bond | 4-quinolyl |
| 63 | nonyl | bond | 2-thiazolyl |
| 64 | decyl | bond | 3-furyl |
| 65 | 1,1,dimethyl-propyl | bond | phenyl |
| 66 | ethenyl | bond | cyclohexyl |
| 67 | prop-2-enyl | bond | 3-bromocyclohexyl |
| 68 | phenyl | bond | adamantyl |
| 69 | naphthyl | bond | 4-indolyl |
| 70 | 4-nitrophenyl | bond | 2-imidazolyl |
| 71 | 4-hydroxy-phenyl | bond | 1-naphthyl |
| 72 | 4-chlorophenyl | bond | 4-nitrophenyl |
| 73 | 4-methylphenyl | bond | 4-hydroxyphenyl |
| 74 | 4-methoxy-phenyl | bond | 3-piperidyl |
| 75 | 4-dimethyl-amino-phenyl | bond | 3,4,5-trimethyl-phenyl |
| 76 | phenyl-ethyl-phenyl | bond | 3-pyridyl |
| 77 | 4-nitro-3-hydroxy-phenyl | bond | 3,4,5-trifluoro-phenyl |
| 78 | 1-pyridyl | bond | 1-pyrrolidyl |
| 79 | 1-piperidyl | bond | 4-phenylazo-phenyl |
| 80 | 1-pyrrolidyl | 2-bromo-propyl | 4-amino-3-hydroxy-phenyl |
| 81 | cyclohexyl | prop-2-enyl | 3,4,5-triamino-phenyl |
| 82 | cyclopentyl | methyl | 4-hydroxyphenyl |
| 83 | adamantyl | ethyl | phenyl |
| 84 | benzyl | i-propyl | 9-anthracenyl |
| 85 | 4-hydroxy-benzyl | n-propyl | 4-pyrenyl |
| 86 | 3,4,5-trihydroxy-phenyl | 2-imino-propyl | 3-furyl |
| 87 | thiazolyl | 2-thio-propyl | 3-thiophenyl |
| 88 | 2-phenylethyl | 2-sulfonyl-propyl | 4-pyrimidinyl |
| 89 | 3-phenylpropyl | ethenyl | 4-isoquinolyl |
| 90 | 2-phenyl-ethenyl | bond | 4-sulfonylphenyl |
| 91 | 3-phenylprop-2-enyl | chloro-methyl | 4-imino-phenyl |
| 92 | 3-bromopropyl | —CH$_2$—N=CH— | 4-phenylethoxy-phenyl |
| 93 | 4-fluoro-n-butyl | —CH$_2$—S—CH$_2$— | 4-ethylphenoxy-phenyl |
| 94 | 3-methoxy-propyl | —CH$_2$—NH—CH$_2$— | 4-phenoxy-phenyl |
| 95 | 2-hydroxyethyl | —CH$_2$—O—CH$_2$— | 3-phenylpropyl-phenyl |
| 96 | tert-butyl | —CH$_2$— | 2-thienyl |
| 97 | tert-butyl | bond | 2-chloro-phenyl |
| 98 | tert-butyl | bond | 4-chloro-phenyl |
| 99 | tert-butyl | bond | 3,4,5-trimethoxy-phenyl |
| 100 | tert-butyl | bond | 3-(phenylthio)-pyridinyl |
| 101 | tert-butyl | bond | 3-(2-fluoro-6-chlorophenyl)-5-methyl-isoxazolyl |
| 102 | tert-butyl | —O—CH$_2$—, X attaches directly to the CH$_2$ | phenyl |

Example 4

Approximate IC$_{50}$ Data for Selected Compounds

The IC$_{50}$ of with respect to PARP inhibition was determined for several compounds by a PARP assay using purified recombinant human PARP from Trevigen (Gaithersburg, Md.), as follows: The PARP enzyme assay was set up on ice in a volume of 100 microliters consisting of 10 mM Tris-HCl (pH 8.0), 1 mM MgCl$_2$, 28 mM KCl, 28 mM NaCl, 0.1 mg/ml of herring sperm DNA (activated as a 1 mg/ml stock for 10 minutes in a 0.15% hydrogen peroxide solution), 3.0 micromolar [3H]nicotinamide adenine dinucleotide (470 mci/mmole), 7 micrograms/ml PARP enzyme, and various concentrations of the compounds to be tested. The reaction was initiated by incubating the mixture at 25° C. After 15 minutes' incubation, the reaction was terminated by adding 500 microliters of ice cold 20% (w/v) trichloroacetic acid. The precipitate formed was transferred onto a glass fiber filter (Packard Unifilter-GF/B) and washed three times with ethanol. After the filter was dried, the radioactivity was determined by scintillation counting.

Using the PARP assay described above, approximate $IC_{50}$ values were obtained for the following compounds:

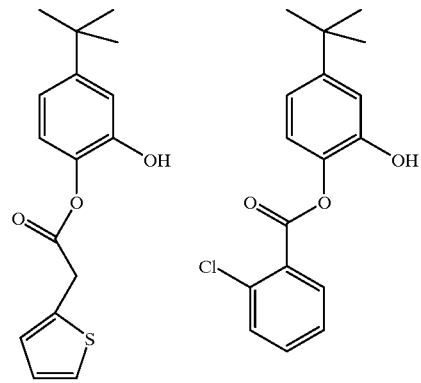

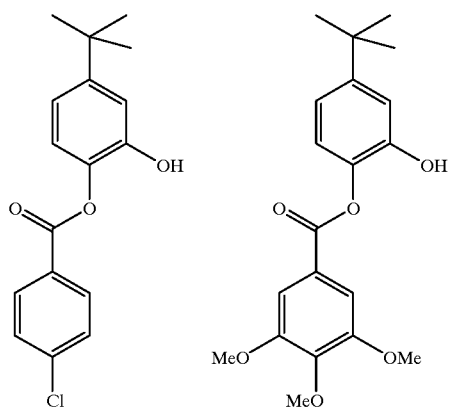

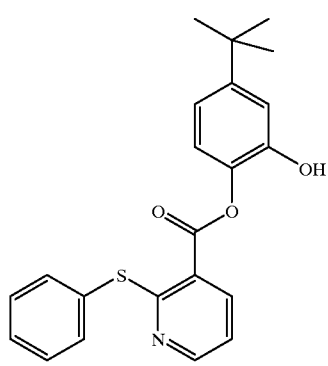

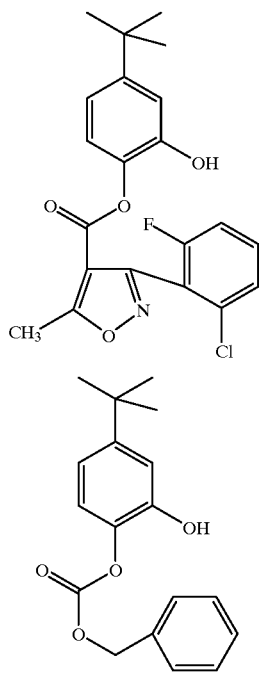

The compounds have an $IC_{50}$ for inhibiting poly(ADP-ribose) synthase in vitro of preferably 50 μM or lower, more preferably 25 μM or lower, and most preferably 10 μM or lower. Similar $IC_{50}$ values are obtained for the other ortho-diphenol compounds of the invention.

Example 5

Neuroprotective Effect of DPQ on Focal Cerebral Ischemia in Rats

Focal cerebral ischemia was produced by cauterization of the right distal MCA (middle cerebral artery) with bilateral temporary common carotid artery occlusion in male Long-Evans rats for 90 minutes. All procedures performed on the animals were approved by the University Institutional Animal Care and Use Committee of the University of Pennsylvania. A total of 42 rats (weights: 230–340 g) obtained from Charles River were used in this study. The animals fasted overnight with free access to water prior to the surgical procedure.

Two hours prior to MCA occlusion, varying amounts (control, n=14; 5 mg/kg, n=7; 10 mg/kg, n=7; 20 mg/kg, n=7; and 40 mg/kg, n=7) of the compound, 3,4-dihydro-5-[4-(1-piperidinyl)-butoxy]-1(2H)-isoquinolinone ("DPQ") were dissolved in dimethyl sulfoxide (DMSO) using a sonicator. A volume of 1.28 ml/kg of the resulting solution was injected intraperitoneally into fourteen rats.

The rats were then anesthetized with halothane (4% for induction and 0.8%–1.2% for the surgical procedure) in a mixture of 70% nitrous oxide and 30% oxygen. The body temperature was monitored by a rectal probe and maintained at 37.5±0.5° C. with a heating blanket regulated by a homeothermic blanket control unit (Harvard Apparatus Limited, Kent, U.K.). A catheter (PE-50) was placed into the tail artery, and arterial pressure was continuously monitored and recorded on a Grass polygraph recorder (Model 7D, Grass Instruments, Quincy, Mass.). Samples for blood gas analysis (arterial pH, $PaO_2$ and $PaCO_2$) were also taken from the tail artery catheter and measured with a blood gas analyzer (ABL 30, Radiometer, Copenhagen, Denmark). Arterial blood samples were obtained 30 minutes after MCA occlusion.

The head of the animal was positioned in a stereotaxic frame, and a right parietal incision between the right lateral canthus and the external auditory meatus was made. Using a dental drill constantly cooled with saline, a 3 mm burr hole was prepared over the cortex supplied by the right MCA, 4 mm lateral to the sagittal suture and 5 mm caudal to the coronal suture. The dura mater and a thin inner bone layer were kept, care being taken to position the probe over a tissue area devoid of large blood vessels. The flow probe (tip diameter of 1 mm, fiber separation of 0.25 mm) was lowered to the bottom of the cranial burr hole using a micromanipulator. The probe was held stationary by a probe holder secured to the skull with dental cement. The microvascular blood flow in the right parietal cortex was continuously monitored with a laser Doppler flowmeter (FloLab, Moor, Devon, U.K., and Periflux 4001, Perimed, Stockholm, Sweden).

Focal cerebral ischemia was produced by cauterization of the distal portion of the right MCA with bilateral temporary common carotid artery (CCA) occlusion by the procedure of Chen et al., "A Model of Focal Ischemic Stroke in the Rat: Reproducible Extensive Cortical Infarction", *Stroke* 17:738–43 (1986) and/or Liu et al., "Polyethylene Glycol-conjugated Superoxide Dismutase and Catalase Reduce Ischemic Brain Injury", *Am. J. Physiol.* 256:H589–93 (1989), both of which are hereby incorporated by reference.

Specifically, bilateral CCA's were isolated, and loops made from polyethylene (PE-10) catheter were carefully passed around the CCA's for later remote occlusion. The incision made previously for placement of the laser doppler probe was extended to allow observation of the rostral end of the zygomatic arch at the fusion point using a dental drill, and the dura mater overlying the MCA was cut. The MCA distal to its crossing with the inferior cerebral vein was lifted by a fine stainless steel hook attached to a micromanipulator and, following bilateral CCA occlusion, the MCA was cauterized with an electrocoagulator. The burr hole was covered with a small piece of Gelform, and the wound was sutured to maintain the brain temperature within the normal or near-normal range.

After 90 minutes of occlusion, the carotid loops were released, the tail arterial catheter was removed, and all of the wounds were sutured. Gentamicin sulfate (10 mg/ml) was topically applied to the wounds to prevent infection. The anesthetic was discontinued, and the animal was returned to his cage after awakening. Water and food were allowed ad libitum.

Two hours after MCA occlusion, the animals were given the same doses of the PARP inhibitor as in the pre-treatment. Twenty-four hours after MCA occlusion, the rats were sacrificed with an intraperitoneal injection of pentobarbital sodium (150 mg/kg). The brain was carefully removed from the skull and cooled in ice-cold artificial CSF for five minutes. The cooled brain was then sectioned in the coronal plane at 2 mm intervals using a rodent brain matrix (RBM-4000C, ASI Instruments, Warren, Mich.). The brain slices were incubated in phosphate-buffered saline containing 2% 2,3,5-triphenyltetrazolium chloride (TTC) at 37° C. for ten minutes. Color photographs were taken of the posterior surface of the stained slices and were used to determine the damaged area at each cross-sectional level using a computer-based image analyzer (NIH Image 1.59). To avoid artifacts due to edema, the damaged area was calculated by subtracting the area of the normal tissue in the hemisphere ipsilateral to the stroke from the area of the hemisphere contralateral to the stroke, by the method of Swanson et al., "A Semiautomated Method for Measuring Brain Infarct Volume", *J. Cereb. Blood Flow Metabol.* 10:290–93 (1990), the disclosure of which is hereby incorporated by reference. The total volume of infarction was calculated by summation of the damaged volume of the brain slices.

The cauterization of the distal portion of the right MCA with bilateral temporary CCA occlusion consistently produced a well-recognized cortical infarct in the right MCA territory of each test animal. There was an apparent uniformity in the distribution of the damaged area as measured by TTC staining in each group, as shown in FIG. 1.

In FIG. 1, the distribution of the cross-sectional infarct area at representative levels along the rostrocaudal axis was measured from the interaural line in non-treated animals and in animals treated with 10 mg/kg of 3,4-dihydro-5-[4-(1-piperidinyl)-butoxy]-1(2H)-isoquinolinone. The area of damage was expressed as mean ± standard deviation. Significant differences between the 10 mg-treated group and the control group were indicated (*$p<0.02$, $p<0.01$, $p<0.001$). The 5 mg/kg and 20 mg/kg curves fell approximately halfway between the control and the 10 mg/kg curves, whereas the 40 mg/kg curve was close to the control. The 5, 20 and 40 mg/kg curves were omitted for clarity.

PARP inhibition led to a significant decrease in the damaged volume in the 5 mg/kg-treated group (106.7±23.2 $mm^3$, $p<0.001$), the 10 mg/kg-treated group (76.4±16.8 $mm^3$, $p<0.0001$), and the 20 mg/kg-treated group (110.2±42.0 $mm^3$, $p<0.01$), compared to the control group (165.2±34.0 $mm^3$). The data are expressed as mean ± standard deviation. The significance of differences between groups was determined using an analysis of variance (ANOVA) followed by Student's t-test for individual comparisons.

There was no significant difference between the control and the 40 mg/kg-treated group (135.6±44.8 $mm^3$). However, there were significant differences between the 5 mg/kg-treated group and the 10 mg/kg-treated group ($p<0.02$), and between the 10 mg/kg-treated group and the 40 mg/kg-treated group ($p<0.01$), as shown in FIG. 2.

Figure 2:
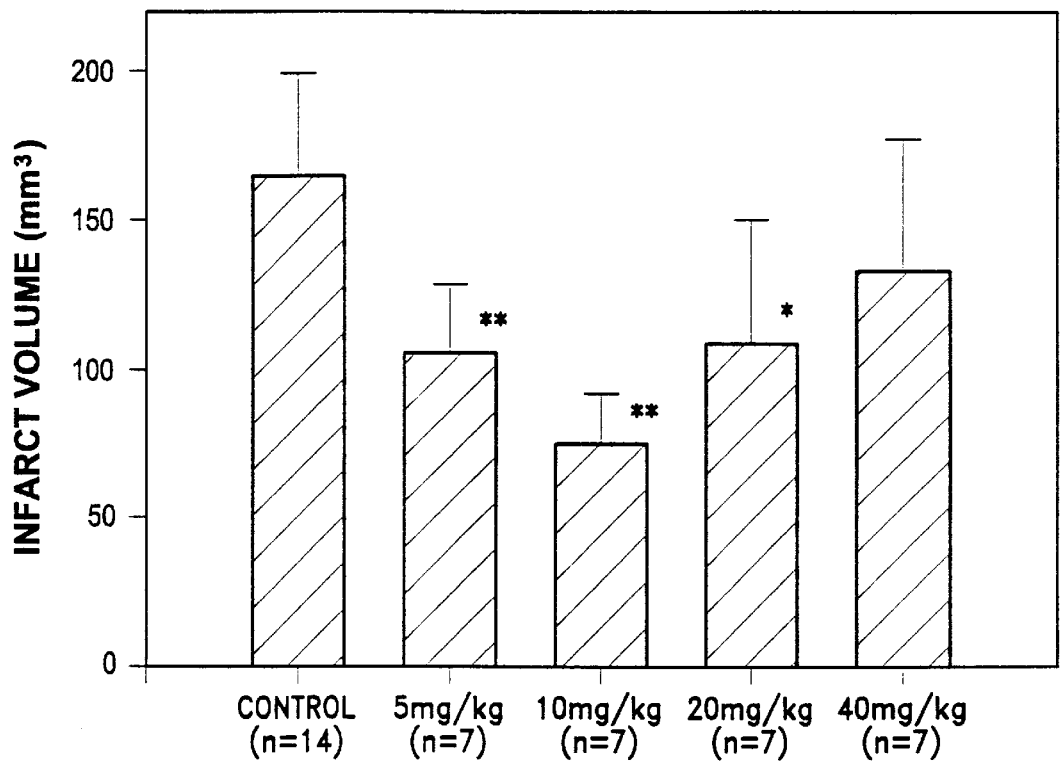
FIG. 2 shows the effect of intraperitoneal administration of 3,4-dihydro-5-[4-(1-piperidinyl)-butoxy]-1(2H)-isoquinolinone on the infarct volume.

In FIG. 2, the effect of intraperitoneal administration of 3,4-dihydro-5-[4-(1-piperidinyl)-butoxy]-1(2H)-isoquinolinone on the infarct volume was depicted graphically. The volumes of infarct were expressed as mean ± standard deviation. Significant differences between the treated groups and the control group were indicated (*$p<0.01$, **$p<0.001$). It is not clear why a high dose (40 mg/kg) of the PARP inhibitor, 3,4-dihydro-5-[4-(1-piperidinyl)-butoxy]-1(2H)-isoquinolinone, was less neuroprotective. The U-shaped dose-response curve may suggest dual effects of the compound.

However, overall, the in vivo administration of the inhibitor led to a substantial reduction in infarct volume in the focal cerebral ischemia model in the rat. This result indicated that the activation of PARP plays an important role in the pathogenesis of brain damage in cerebral ischemia.

The values of arterial blood gases ($PaO_2$, $PaCO_2$ and pH) were within the physiological range in the control and treated groups with no significant differences in these parameters among the five groups, as shown below in Table 2. A "steady state" MABP was taken following completion of the surgical preparation, just prior to occlusion; an "ischemia" MABP was taken as the average MABP during occlusion. See Table III below:

TABLE III

| | $PaO_2$ (mm Hg) | $PaCO_2$ (mm Hg) | pH | MABP (mm Hg) | |
| --- | --- | --- | --- | --- | --- |
| | | | | Steady State | Ischemia |
| Control group (n = 4) | 125 ± 21 | 38.6 ± 4.6 | 7.33 ± 0.05 | 79 ± 14 | 91 ± 13** |
| 5 mg/kg-treated group (n = 7) | 126 ± 20 | 38.0 ± 2.8 | 7.36 ± 0.02 | 78 ± 5 | 91 ± 12** |
| 10 mg/kg-treated group (n = 7) | 125 ± 16 | 39.3 ± 5.2 | 7.34 ± 0.03 | 80 ± 9 | 90 ± 14* |
| 20 mg/kg-treated group (n = 7) | 122 ± 14 | 41.3 ± 2.8 | 7.35 ± 0.23 | 79 ± 10 | 91 ± 12** |
| 40 mg/kg-treated group (n = 7) | 137 ± 17 | 39.5 ± 4.7 | 7.33 ± 0.24 | 78 ± 4 | 88 ± 12* |

*Significantly different from the steady state value, p < 0.05.
**Significantly different from the steady state value, p < 0.01.

There were no significant differences in any physiological parameter, including mean arterial blood pressure (MABP), prior to MCA and CCA occlusion among the five groups. Although MABP was significantly elevated following occlusion in all five groups, there were no significant differences in MABP during the occlusion period among the groups.

Since the blood flow values obtained from the laser doppler were in arbitrary units, only percent changes from the baseline (prior to occlusion) were reported. Right MCA and bilateral CCA occlusion produced a significant decrease in relative blood flow in the right parietal cortex to 20.8±7.7% of the baseline in the control group (n=5), 18.7±7.4% in the 5 mg/kg-treated group (n=7), 21.4±7.7% in the 10 mg/kg-treated group (n=7) and 19.3±11.2% in the 40 mg/kg-treated group (n=7). There were no significant differences in the blood flow response to occlusion among the four groups. In addition, blood flow showed no significant changes throughout the entire occlusion period in any group.

Following release of the carotid occlusions, a good recovery of blood flow (sometimes hyperemia) was observed in the right MCA territory of all animals. Reperfusion of the ischemic tissue resulted in the formation of NO and peroxynitrite, in addition to oxygen-derived free radicals. All of these radicals have been shown to cause DNA strand breaks and to activate PARP.

This example provided evidence that the related compounds of the present invention are effective in inhibiting PARP activity.

Example 6

Assay for Neuroprotective Effects on Focal Cerebral Ischemia in Rats

Focal cerebral ischemia experiments are performed using male Wistar rats weighing 250–300 g, which are anesthe-tized with 4% halothane. Anesthesia is maintained with 1.0–1.5% halothane until the end of surgery. The animals are installed in a warm environment to avoid a decrease in body temperature during surgery.

An anterior midline cervical incision is made. The right common carotid artery (CCA) is exposed and isolated from the vagus nerve. A silk suture is placed and tied around the CCA in proximity to the heart. The external carotid artery (ECA) is then exposed and ligated with a silk suture. A puncture is made in the CCA and a small catheter (PE 10, Ulrich & Co., St-Gallen, Switzerland) is gently advanced to the lumen of the internal carotid artery (ICA). The pterygopalatine artery is not occluded. The catheter is tied in place with a silk suture. Then, a 4-0 nylon suture (Braun Medical, Crissier, Switzerland) is introduced into the catheter lumen and is pushed until the tip blocks the anterior cerebral artery. The length of catheter into the ICA is approximately 19 mm from the origin of the ECA. The suture is maintained in this position by occlusion of the catheter with heat. One cm of catheter and nylon suture are left protruding so that the suture can be withdrawn to allow reperfusion. The skin incision is then closed with wound clips.

The animals are maintained in a warm environment during recovery from anesthesia. Two hours later, the animals are re-anesthetized, the clips are discarded, and the wound is re-opened. The catheter is cut, and the suture is pulled out. The catheter is then obturated again by heat, and wound clips are placed on the wound. The animals are allowed to survive for 24 hours with free access to food and water. The rats are then sacrificed with $CO_2$ and decapitated.

The brains are immediately removed, frozen on dry ice and stored at −80° C. The brains are then cut in 0.02 mm-thick sections in a cryocut at −19° C., selecting one of every 20 sections for further examination. The selected sections are stained with cresyl violet according to the Nissl procedure. Each stained section is examined under a light microscope, and the regional infarct area is determined according to the presence of cells with morphological changes.

Various doses of the compounds of the invention are tested in this model. The compounds are administered in either a single dose or a series of multiple doses, i.p. or i.v., at different times, both before or after the onset of ischemia. Compounds of the invention are found to provide protection from ischemia in the range of about 20 to 80%.

Example 7

Effects on Heart Ischemia/Reperfusion Injury in Rats

Female Sprague-Dawley rats, each weighing about 300–350 g are anesthetized with intraperitoneal ketamine at a dose of 150 mg/kg. The rats are endotracheally intubated and ventilated with oxygen-enriched room air using a Harvard rodent ventilator. Polyethylene catheters inserted into the carotid artery and the femoral vein are used for artery blood pressure monitoring and fluid administration respectively. Arterial $pCO_2$ is maintained between 35 and 45 mm Hg by adjusting the respirator rate. The rat chests are opened by median sternotomy, the pericardium is incised, and the hearts are cradled with a latex membrane tent. Hemodynamic data are obtained at baseline after at least a 15-minute stabilization period following the end of the surgical operation. The LAD (left anterior descending) coronary artery is ligated for 40 minutes, and then re-perfused for 120 minutes.

After 120 minutes' reperfusion, the LAD artery is re-occluded, and a 0.1 ml bolus of monastral blue dye is injected into the left atrium to determine the ischemic risk region.

The hearts are then arrested with potassium chloride and cut into five 2–3 mm thick transverse slices. Each slice is weighed and incubated in a 1% solution of trimethyltetrazolium chloride to visualize the infarcted myocardium located within the risk region. Infarct size is calculated by summing the values for each left ventricular slice and is further expressed as a fraction of the risk region of the left ventricle.

Various doses of the compounds of the invention are tested in this model. The compounds are given either in a single dose or a series of multiple doses, i.p. or i.v., at different times, both before or after the onset of ischemia. The compounds of the invention are found to have ischemia/reperfusion injury protection in the range of 10 to 40 percent. Therefore, they protect against ischemia-induced degeneration of rat hippocampal neurons in vitro.

Example 8

Retinal Ischemia Protection

A patient just diagnosed with acute retinal ischemia is immediately administered parenterally, either by intermittent or continuous intravenous administration, a compound of formula I, either as a single dose or a series of divided doses of the compound. After this initial treatment, and depending on the patient's presenting neurological symptoms, the patient optionally may receive the same or a different compound of the invention in the form of another parenteral dose. It is expected by the inventors that significant prevention of neural tissue damage would ensue and that the patient's neurological symptoms would considerably lessen due to the administration of the compound, leaving fewer residual neurological effects post-stroke. In addition, it is expected that the re-occurrence of retinal ischemia would be prevented or reduced.

Example 9

Treatment of Retinal Ischemia

A patient has just been diagnosed with acute retinal ischemia. Immediately, a physician or a nurse parenterally administers a compound of formula I, either as a single dose or as a series of divided doses. The patient also receives the same or a different PARP inhibitor by intermittent or continuous administration via implantation of a biocompatible, biodegradable polymeric matrix delivery system comprising a compound of formula I, or via a subdural pump inserted to administer the compound directly to the infarct area of the brain. It is expected by the inventors that the patient would awaken from the coma more quickly than if the compound of the invention were not administered. The treatment is also expected to reduce the severity of the patient's residual neurological symptoms. In addition, it is expected that re-occurrence of retinal ischemia would be reduced.

Example 10

Vascular Stroke Protection

A patient just diagnosed with acute vascular stroke is immediately administered parenterally, either by intermittent or continuous intravenous administration, a compound of formula I, either as a single dose or a series of divided doses of the compound. After this initial treatment, and depending on the patient's presenting neurological symptoms, the patient optionally may receive the same or a different compound of the invention in the form of another parenteral dose. It is expected by the inventors that significant prevention of neural tissue damage would ensue and that the patient's neurological symptoms would considerably lessen due to the administration of the compound, leaving fewer residual neurological effects post-stroke. In addition, it is expected that the re-occurrence of vascular stroke would be prevented or reduced.

Example 11

Treatment of Vascular Stroke

A patient has just been diagnosed with acute multiple vascular strokes and is comatose. Immediately, a physician or a nurse parenterally administers a compound of formula I, either as a single dose or as a series of divided doses. Due to the comatose state of the patient, the patient also receives the same or a different PARP inhibitor by intermittent or continuous administration via implantation of a biocompatible, biodegradable polymeric matrix delivery system comprising a compound of formula I, or via a subdural pump inserted to administer the compound directly to the infarct area of the brain. It is expected by the inventors that the patient would awaken from the coma more quickly than if the compound of the invention were not administered. The treatment is also expected to reduce the severity of the patient's residual neurological symptoms. In addition, it is expected that re-occurrence of vascular stroke would be reduced.

Example 12

Preventing Cardiac Reperfusion Injury

A patient is diagnosed with life-threatening cardiomyopathy and requires a heart transplant. Until a donor heart is found, the patient is maintained on Extra Corporeal Oxygenation Monitoring (ECMO).

A donor heart is then located, and the patient undergoes a surgical transplant procedure, during which the patient is placed on a heart-lung pump. The patient receives a compound of the invention intracardiac within a specified period of time prior to re-routing his or her circulation from the heart-lung pump to his or her new heart, thus preventing cardiac reperfusion injury as the new heart begins to beat independently of the external heart-lung pump.

Example 13

Septic Shock Assay

Groups of 10 C57/BL male mice weighing 18 to 20 g were administered a test compound, 1-carboxynaphthalene-1-carboxamide at the doses of 60, 20, 6 and 2 mg/kg, daily, by intraperitoneal (IP) injection for three consecutive days. Each animal was first challenged with lipopolysaccharide (LPS, from *E. Coli*, $LD_{100}$ of 20 mg/animal IV) plus galactosamine (20 mg/animal IV). The first dose of test compound in a suitable vehicle was given 30 minutes after challenge, and the second and third doses were given 24 hours later on day 2 and day 3 respectively, with only the surviving animals receiving the second or third dose of the test compound. Mortality was recorded every 12 hours after challenge for the three-day testing period. 1-Carboxynaphthalene-1-carboxamide provided a protection against mortality from septic shock of about 40%. Based on these results, other compounds of the invention are expected to provide a protection against mortality exceeding about 35%.

Example 14

Inhibition of PARP Activity

A patient has just been diagnosed with a disorder requiring the administration of a PARP inhibitor. A physician or a nurse parenterally administers a compound of formula I, either as a single dose or as a series of divided doses. The patient may receive the same or a different PARP inhibitor by intermittent or continuous administration via implantation of a biocompatible, biodegradable polymeric matrix delivery system comprising a compound of formula I, or via a subdural pump inserted to administer the compound directly to the desired treatment location. It would be expected that the treatment would alleviate the disorder, either in part or in its entirety and that no further occurrences of the disorder would develop.

Example 15

A treatment such as that described in Example 14 wherein the patient is diagnosed with a peripheral neuropathy caused by physical injury or a disease state.

Example 16

A treatment such as that described in Example 14 wherein the patient is diagnosed with Guillain-Barre syndrome.

Example 17

A treatment such as that described in Example 14 wherein the patient is diagnosed with traumatic brain injury.

Example 18

A treatment such as that described in Example 14 wherein the patient is diagnosed with physical damage to the spinal cord.

Example 19

A treatment such as that described in Example 14 wherein the patient is diagnosed with stroke associated with brain damage.

Example 20

A treatment such as that described in Example 14 wherein the patient is diagnosed with focal ischemia.

Example 21

A treatment such as that described in Example 14 wherein the patient is diagnosed with global ischemia.

Example 22

A treatment such as that described in Example 14 wherein the patient is diagnosed with reperfusion injury.

Example 23

A treatment such as that described in Example 14 wherein the patient is diagnosed with a demyelinating disease.

Example 24

A treatment such as that described in Example 14 wherein the patient is diagnosed with multiple sclerosis.

Example 25

A treatment such as that described in Example 14 wherein the patient is diagnosed with a neurological disorder relating to neurodegeneration.

Example 26

A treatment such as that described in Example 14 wherein the patient is diagnosed with Alzheimer's Disease.

Example 27

A treatment such as that described in Example 14 wherein the patient is diagnosed with Parkinson's Disease.

Example 28

A treatment such as that described in Example 14 wherein the patient is diagnosed with amyotrophic lateral sclerosis.

Example 29

A treatment such as that described in Example 14 wherein the patient is diagnosed with a cardiovascular disease.

Example 30

A treatment such as that described in Example 14 wherein the patient is diagnosed with angina pectoris.

Example 31

A treatment such as that described in Example 14 wherein the patient is diagnosed with myocardial infarction.

Example 32

A treatment such as that described in Example 14 wherein the patient is diagnosed with cardiovascular tissue damage related to PARP activation.

Example 33

In vitro Radiosensitization

The human prostate cancer cell line, PC-3s, were plated in 6 well dishes and grown at monolayer cultures in RPMI1640 supplemented with 10% FCS. The cells are maintained at 37° C. in 5% $CO_2$ and 95% air. The cells were exposed to a dose response (0.1 mM to 0.1 $\mu$M) of 3 different PARP inhibitors of Formula I disclosed herein prior to irradiation at one sublethal dose level. For all treatment groups, the six well plates were exposed at room temperature in a Seifert 250 kV/15 mA irradiator with a 0.5 mm Cu/1 mm. Cell viability was examined by exclusion of 0.4% trypan blue. Dye exclusion was assessed visually by microscopy and viable cell number was calculated by subtracting the number of cells from the viable cell number and dividing by the total number of cells. Cell proliferation rates were calculated by the amount of $^3$H-thymidine incorporation post-irradiation. The PARP inhibitors show radiosensitization of the cells.

Example 34

In vivo Radiosensitization

Before undergoing radiation therapy to treat cancer, a patient is administered an effective amount of a compound or a pharmaceutical composition of the present invention. The compound or pharmaceutical composition acts as a radiosensitizer and making the tumor more susceptible to radiation therapy.

Example 35

Measuring Altered Gene Expression in mRNA Senescent Cells

Human fibroblast BJ cells, at Population Doubling (PDL) 94, are plated in regular growth medium and then changed to low serum medium to reflect physiological conditions described in Linskens, et al., *Nucleic Acids Res.* 23:16:3244–3251 (1995). A medium of DMEM/199 wupplemented with 0.5% bovine calf serum is used. The cells are treated daily for 13 days with the PARP inhibitor of Formula I. The control cells are treated with and without the solvent used to administer the PARP inhibitor. The untreated old and young control cells are tested for comparison. RNA is prepared from the treated and control cells according to the techniques described in PCT Publication No. 96/13610 and Northern blotting is conducted. Probes specific for senescence-related genes are analyzed, and treated and control cells compared. In analyzing the results, the lowest level of gene expression is arbitrarily set at 1 to provide a basis for comparison. Three genes particularly relevant to age-related changes in the skin are collagen, collagenase and elastin. West, *Arch. Derm.* 130:87–95 (1994). Elastin expression of the cells treated with the PARP inhibitor of Formula I is significantly increased in comparison with the control cells. Elastin expression is significantly higher in young cells compared to senescent cells, and thus treatment with the PARP inhibitor of Formula I causes elastin expression levels in senescent cells to change to levels similar to those found in much younger cells. Similarly, a beneficial effect is seen in collagenase and collagen expression with treatment with the PARP inhibitors of Formula I.

Example 36

Measuring Altered Gene Expression Protein in Senescent Cells

Approximately 105 BJ cells, at PDL 95–100 are plated and grown in 15 cm dishes. The growth medium is DMEM/199 supplemented with 10% bovice calf serum. The cells are treated daily for 24 hours with the PARP inhibitors of Formula I (100 $\mu$g/1 mL of medium). The cells are washed with phosphate buffered solution (PBS), then permeablized with 4% paraformaldehyde for 5 minutes, then washed with PBS, and treated with 100% cold methanol for 10 minutes. The methanol is removed and the cells are washed with PBS, and then treated with 10% serum to block nonspecific antibody binding. About 1 mL of the appropriate commercially available antibody solutions (1:500 dilution. Vector) is added to the cells and the mixture incubated for 1 hour. The cells are rinsed and washed three times with PBS. A secondary antibody, goat anti-mouse IgG (1 mL) with a biotin tag is added along with 1 mL of a solution containing streptavidin conjugated to alkaline phosphatase and 1 mL of NBT reagent (Vector). The cells are washed and changes in gene expression are noted colorimetrically. Four senescence-specific genes—collagen I, collagen III, collagenase, and interferon gamma—in senescent cells treated with the PARP inhibitor of Formula I are monitored and the results show a decrease in interferon gamma expression with no observable change in the expression levels of the other three gens, demonstrating that the PARP inhibitors of Formula I can alter senescence-specific gene expression.

Example 37

Extending or Increasing Proliferative Capacity and Lifespan of Cells

To demonstrate the effectiveness of the present method for extending the proliferative capacity and lifespan of cells, human fibroblast cells lines (either W138 at Population Doubling (PDL) 23 or BJ cells at PDL 71) are thawed and plated on T75 flasks and allowed to grow in normal medium (DMEM/M199 plus 10% bovine calf serum) for about a week, at which time the cells are confluent, and the cultures are therefor ready to be subdivided. At the time of subdivision, the media is aspirated, and the cells rinsed with phosphate buffer saline (PBS) and then trypsinized. The cells are counted with a Coulter counter and plated at a density of $10^5$ cells per cm$^2$ in 6-well tissue culture plates in DMEM/199 medium supplemented with 10% bovine calf serum and varying amounts (0.10 $\mu$M, and 1 mM: from a 100× stock solution in DMEM/M199 medium) of a PARP inhibitor of Formula I as disclosed herein. This process is repeated every 7 days until the cell appear to stop dividing. The untreated (control) cells reach senescence and stop dividing after about 40 days in culture. Treatment of cells with 10 $\mu$M 3-AB appears to have little or no effect in contrast to treatment with 100 $\mu$M 3-AB which appears lengthen the lifespan of the cells and treatment with 1 mM 3-AB which dramatically increases the lifespan and proliferative capacity of the cells. The cells treated with 1 mM 3-AB will still divide after 60 days in culture.

Example 38

Neuroprotective Effects on Chronic Constriction Injury (CCI) in Rats

Adult male Sprague-Dawley rats, 300–350 g, are anesthetized with intraperitoneal 50 mg/kg sodium pentobarbital. Nerve ligation is performed by exposing one side of the rat's sciatic nerves and dissecting a 5–7 mm-long nerve segment and closing with four loose ligatures at a 1.0–1.5-mm, followed by implanting of an intrathecal catheter and inserting of a gentamicin sulfate-flushed polyethylene (PE-10) tube into the subarachnoid space through an incision at the cisterna magna. The caudal end of the catheter is gently threaded to the lumbar enlargement and the rostral end is secured with dental cement to a screw embedded in the skull and the skin wound is closed with wound clips.

Thermal hyperalgesia to radiant heat is assessed by using a paw-withdrawal test. The rat is placed in a plastic cylinder on a 3-mm thick glass plate with a radiant heat source from a projection bulb placed directly under the plantar surface of the rat's hindpaw. The paw-withdrawal latency is defined as the time elapsed from the onset of radiant heat stimulation to withdrawal of the rat's hindpaw.

Mechanical hyperalgesia is assessed by placing the rat in a cage with a bottom made of perforated metal sheet with many small square holes. Duration of paw-withdrawal is recorded after pricking the mid-plantar surface of the rat's hindpaw with the tip of a safety pin inserted through the cage bottom.

Mechano-allodynia is assessed by placing a rat in a cage similar to the previous test, and applying von Frey filaments in ascending order of bending force ranging from 0.07 to 76 g to the mid-plantar surface of the rat's hindpaw. A von Frey filament is applied perpendicular to the skin and depressed slowly until it bends. A threshold force of response is defined as the first filament in the series to evoke at least one clear paw-withdrawal out of five applications.

Dark neurons are observed bilaterally within the spinal cord dorsal horn, particularly in laminae I–II, of rats 8 days after unilateral sciatic nerve ligation as compared with sham operated rats. Various doses of differing compounds of Formula I tested in this model and show that the Formula I compounds reduce both incidence of dark neurons and neuropathic pain behavior in CCI rats.

The invention being thus described, it will be obvious that the same may be varied in many ways. Such variations are not to be regarded as a departure from the spirit and scope of the invention, and all such modifications are intended to be included within the scope of the following claims.

We claim:

1. A compound of formula (I):

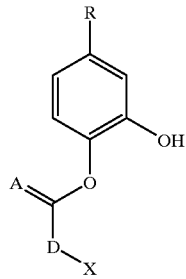

I or a pharmaceutically acceptable salt, hydrate, ester, solvate, prodrug, stereoisomer, or mixtures thereof, wherein A is O or S;

R is $C_1$–$C_{10}$ straight or branched chain alkyl, $C_2$–$C_{10}$ straight or branched chain alkenyl, aryl, or carbocycle;

D is a bond, or a $C_1$–$C_3$ straight or branched chain alkyl, $C_2$–$C_3$ straight or branched chain alkenyl, $C_2$–$C_3$ straight or branched chain alkynyl, wherein any of the carbon atoms of said alkyl, alkenyl, or alkynyl of D are optionally replaced with oxygen, nitrogen, or sulfur; and X is aryl, or carbocycle;

wherein said alkyl, alkenyl, alkynyl, aryl, or carbocycle of R, D, or X is optionally substituted with one or more substituents selected from hydroxy, halo, haloalkyl, thiocarbonyl, alkoxy, alkenoxy, alkylaryloxy, aryloxy, arylalkyloxy, cyano, nitro, amino, imino, alkylamino, arylamino, arylazo, arylthio, aminoalkyl, sulfhydryl, thioalkyl, alkylthio, sulfonyl, $C_1$–$C_6$ straight or branched chain alkyl, $C_2$–$C_6$ straight or branched chain alkenyl or alkynyl, aryl, aralkyl, or carbocycle;

provided that when R is methyl, and D is a bond or $C_2$–$C_3$ straight chain alkenyl, then X is not phenyl, 4-nitrophenyl, 4-phenylazo-phenyl, or 3,5-dinitrophenyl; when R is methyl, and D is $C_2$–$C_3$ straight chain alkenyl, X is not hydroxy substituted phenyl; when R is ethenyl, and D is ethenyl, then X is not 4-hydroxy-3-methoxyphenyl; when R is methyl, and D is ethenyl, then X is not 2-hydroxyphenyl; when R is 1-hydroxy-2-alkylamino-ethyl, and D is a bond, then X is not phenyl, methylphenyl, or 4-methoxyphenyl; and when R is propenyl, and D is a bond, then X is not phenyl.

2. The compound of claim 1, wherein R is a hydrophobic group.

3. The compound of claim 1, wherein R is a $C_1$–$C_{10}$ straight or branched chain alkyl.

4. The compound of claim 1, wherein X is an aryl group.

5. The compound of claim 4, wherein the aryl group is phenyl.

6. The compound of claim 4, wherein said aryl group is substituted selected from the group consisting of halo, hydroxy, amino, nitro, lower alkyl, dimethylamino, acetamide, sulfonyl, aryl, aralkyl, arylthio, —COOR$^1$, —OR$^1$ or —NHR$^1$, where R$^1$ is hydrogen, lower alkyl, and aralkyl.

7. The compound of claim 1, wherein D is a bond.

8. The compound of claim 1, wherein said compound is selected from the group consisting of:

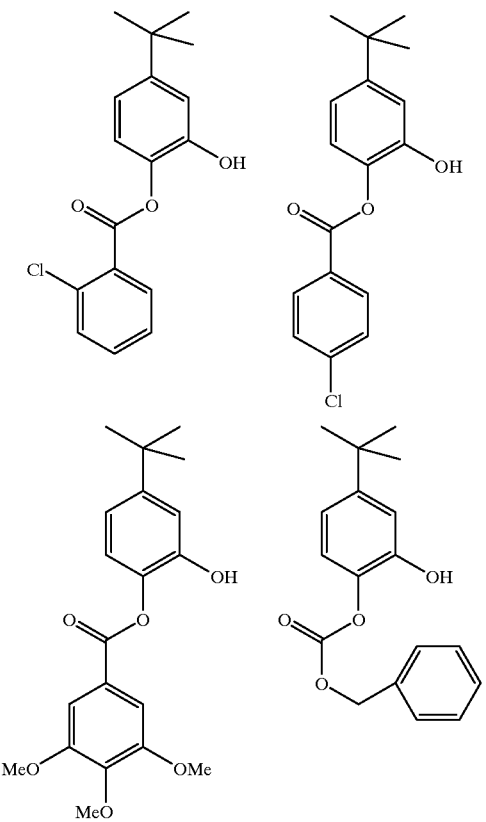

9. A pharmaceutical composition comprising a pharmaceutically acceptable carrier and a compound of formula (I):

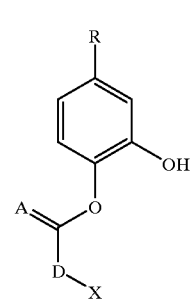

I or a pharmaceutically acceptable salt, hydrate, ester, solvate, prodrug, stercoisomer, or a mixture thereof, wherein A is O or S;

R is $C_1$–$C_{10}$ straight or branched chain alkyl, $C_2$–$C_{10}$ straight or branched chain alkenyl, $C_2$–$C_{10}$ straight or branched chain alkynyl, aryl, or carbocycle;

D is a bond, or a $C_1$–$C_3$ straight or branched chain alkyl, $C_2$–$C_3$ straight or branched chain alkenyl, $C_2$–$C_3$ straight or branched chain alkynyl, wherein any of the carbon atoms of said alkyl, alkenyl, or alkynyl of D are optionally replaced with oxygen, nitrogen, or sulfur; and X is aryl, or carbocycle;

wherein said alkyl, alkenyl, alkynyl, aryl, or carbocycle of R, D, or X is optionally substituted with one or more substituents selected from hydroxy, halo, haloalkyl, thiocarbonyl, alkoxy, alkenoxy, alkylaryloxy, aryloxy, arylalkyloxy, cyano, nitro, amino, imino, alkylamino, arylamino, arylazo, arylthio, aminoalkyl, sulfhydryl, thioalkyl, alkylthio, sulfonyl, $C_1$–$C_6$ straight or branched chain alkyl, $C_2$–$C_6$ straight or branched chain alkenyl or alkynyl, aryl, aralkyl, or carbocycle;

provided that when R is methyl, and D is a bond, then X is not phenyl, 4-nitrophenyl, 4-phenylazo-phenyl, or 3,5-dinitrophenyl; when R is ethenyl, and D is ethenyl, then X is not 4-hydroxy-3-methoxyphenyl; when R is methyl, and D is ethenyl, then X is not 2-hydroxyphenyl; when R is 1-hydroxy-2-alkylamino-ethyl, and D is a bond, then X is not phenyl, methylphenyl, or 4-methoxyphenyl; and when R is propenyl, and D is a bond, then X is not phenyl.

10. The pharmaceutical composition of claim 9, wherein said compound has an $IC_{50}$ of 100 μM or lower for inhibiting poly(ADP-ribose) polymerase in vitro.

11. The pharmaceutical composition of claim 9, wherein said compound has an $IC_{50}$ of 25 μM or lower for inhibiting poly(ADP-ribose) polymerase in vitro.

12. The pharmaceutical composition of claim 9, wherein the carrier is a sterile solution, suspension or emulsion, in a single or divided dose.

13. The pharmaceutical composition of claim 9, wherein the carrier is a capsule or tablet containing a single or divided dose of said compound.

14. The pharmaceutical composition of claim 9, wherein the carrier comprises a biodegradable polymer.

15. The pharmaceutical composition of claim 14, wherein the biodegradable polymer releases the compound of formula I over a prolonged period of time.

16. The pharmaceutical composition of claim 9, wherein the carrier is a solid implant.

17. The pharmaceutical composition of claim 9 for treating diseases and disorders, wherein the diseases or disorders are selected from the group consisting of tissue damage resulting from cell damage or death due to necrosis or apoptosis, neuronal mediated tissue damage or damage or diseases, neural tissue damage resulting from ischemia and reperfusion injury, neurological disorders and neurodegenerative diseases, vascular stroke, cardiovascular disorders, age-related macular degeneration, AIDS, arthritis, atherosclerosis, cachexia, cancer, degenerative diseases of skeletal muscle involving replicative senescence, diabetes, head trauma, immune senescence, inflammatory bowel disorders, muscular dystrophy, osteoarthritis, osteoporosis, chronic pain, acute pain, neuropathic pain, nervous insult, peripheral nerve injury, renal failure, retinal ischemia, septic shock, and skin aging, diseases or disorders relating to lifespan or proliferative capacity of cells, and diseases or disease conditions induced or exacerbated by cellular senescence.

18. The pharmaceutical composition of claim 17, wherein the neurological disorder is selected from the group consisting of peripheral neuropathy caused by physical injury or disease state, traumatic brain injury, physical damage to the spinal cord, stroke associated with brain damage, and demyelinating diseases.

19. The pharmaceutical composition of claim 17, wherein the cardiovascular disorder is selected from the group consisting of cardiovascular tissue damage, coronary artery disease, myocardial infarction, angina pectoris and cardiogenic shock.

20. A method of inhibiting PARP activity or treating diseases or disorders, or radiosensitizing, comprising:
administering a therapeutically effective amount of a compound of formula I:

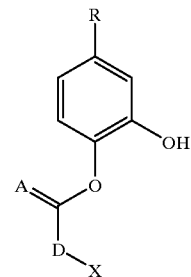

or a pharmaceutically acceptable salt, hydrate, ester, solvate, prodrug, stereoisomer, or mixtures thereof, wherein A is O or S;

R is $C_1$–$C_{10}$ straight or branched chain alkyl, $C_2$–$C_{10}$ straight or branched chain alkenyl, $C_2$–$C_{10}$ straight or branched chain alkynyl, aryl, or carbocycle;

D is a bond, or a $C_1$–$C_3$ straight or branched chain alkyl, $C_2$–$C_3$ straight or branched chain alkenyl, $C_2$–$C_3$ straight or branched chain alkynyl, wherein any of the carbon atoms of said alkyl, alkenyl, or alkynyl of D are optionally replaced with oxygen, nitrogen, or sulfur; and X is aryl, or carbocycle;

wherein said alkyl, alkenyl, alknyl, aryl, or carbocycle of R, D, or X is optionally substituted with one or more substituents selected from hydroxy, halo, haloalkyl, thiocarbonyl, alkoxy, alkenoxy, alkylaryloxy, aryloxy, arylalkyloxy, cyano, nitro, amino, imino, alkylamino, arylamino, arylazo, arylthio, aminoalkyl, sulfhydryl, thioalkyl, alkylthio, sulfonyl, $C_1$–$C_6$ straight or branched chain alkyl, $C_2$–$C_6$ straight or branched chain alkenyl or alkynyl, aryl, aralkyl, or carbocycle;

provided that when R is methyl, and D is a bond, then X is not phenyl, 4-nitrophenyl, 4-phenylazo-phenyl, or 3,5-dinitrophenyl; when R is ethenyl, and D is ethenyl, then X is not 4-hydroxy-3-methoxyphenyl; when R is methyl, and D is ethenyl, then X is not X is not 2-hydroxyphenyl; when R is 1-hydroxy-2-alkylamino-ethyl, and D is a bond, then X is not phenyl, methylphenyl, or 4-methoxyphenyl; and when R is propenyl, and D is a bond, then X is not phenyl.

21. The method of claim 20, wherein the diseases or disorders are selected from the group consisting of tissue damage resulting from cell damage or death due to necrosis or apoptosis, neuronal mediated tissue damage or diseases, neural tissue damage resulting from ischemia and reperfusion injury, neurological disorders and neurodegenerative diseases, vascular stroke, cardiovascular disorders, age-related macular degeneration, AIDS, arthritis, atherosclerosis, cachexia, cancer, degenerative diseases of skeletal muscle involving replicative senescence, diabetes, head trauma, immune senescence, inflammatory bowel disorders, muscular dystrophy, osteoarthritis, osteoporosis, chronic pain, acute pain, neuropathic pain, nervous insult, peripheral nerve injury, renal failure, retinal ischemia, septic shock, and skin aging, diseases or disorders relating to lifespan or proliferative capacity of cells, and diseases or disease conditions induced or exacerbated by cellular senescence.

22. The method of claim 21, wherein the neurological disorder is selected from the group consisting of peripheral neuropathy caused by physical injury or disease state, traumatic brain injury, physical damage to the spinal cord, stroke associated with brain damage, and demyelinating diseases.

23. The method of claim 22, wherein the demyelinating disease is multiple sclerosis.

24. The method of claim 21, wherein the neurodegenerative disease is selected from the group consisting of Alzheimer's Disease, Parkinson's Disease, Huntington's Disease and amyotropic lateral sclerosis.

25. The method of 21, wherein the cancer is selected from the group consisting of ACTH-producing tumors, acute lymphocytic leukemia, acute nonlymphocytic leukemia, cancer of the adrenal cortex, bladder cancer, brain cancer, breat cancer, cervic cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer, malignant peritoneal effusion, malignant pleural effusion, melanoma, mesothelioma, multiple myeloma, neuroblastoma, non-Hodgkin's lymphoma, osteosarcoma, ovary germ cell cancer, prostate cancer, pancreatic cancer, penile cancer, retinoblastoma, skin cancer, soft-tissue sarcoma, squamous cell carcinomas, stomach cancer, testicular cancer, thyroid cancer, trophoblastic neoplasms, cancer of the uterus, vaginal cancer, cancer of the vulva and Wilm's tumor.

26. The method of claim 21, wherein the bowel disorder is colitis.

27. The method of claim 21, wherein the bowel disorder is Crohn's disease.

28. The method of claim 21, wherein the cardiovascular disorder is selected from the group consisting of cardiovascular tissue damage, coronary artery disease, myocardial infarction, angina pectoris and cardiogenic shock.

29. The method of claim 21, wherein the septic shock is endotoxic shock.

30. The method of claim 21, wherein the disease or disease condition induced or exacerbated by cellular senescence is selected from the group consisting of skin aging, Alzheimer's disease, atherosclerosis, osteoarthritis, osteoporosis, muscular dystrophy, age-related macular degeneration, immune senescence, and AIDS.

31. The compound of claim 1 wherein R, A, D and X have the following meaning:

| Compound | R | A | D | X |
|---|---|---|---|---|
| 1 | methyl | O | bond | 4-bromophenyl |
| 2 | ethyl | O | bond | phenyl |
| 3 | n-propyl | O | bond | 3,4,5-trihydroxy-phenyl |
| 4 | i-propyl | O | bond | 3,4,5-trimethoxy-phenyl |
| 5 | n-butyl | O | bond | 3-hydroxyphenyl |
| 6 | t-butyl | O | bond | 4-nitro-naphthyl |
| 7 | s-butyl | O | bond | 3-hydroxy-naphthyl |
| 8 | pentyl | O | bond | benzyl |
| 9 | hexyl | O | bond | 4-ethylphenyl |
| 10 | heptyl | O | bond | 4-ethenylphenyl |
| 14 | 1,1,dimethyl-propyl | O | bond | phenyl |
| 15 | ethenyl | O | bond | cyclohexyl |
| 16 | prop-2-enyl | O | bond | 3-bromocyclohexyl |
| 17 | phenyl | O | bond | adamantyl |
| 20 | 4-hydroxy-phenyl | O | bond | 1-naphthyl |

-continued

| Compound | R | A | D | X |
|---|---|---|---|---|
| 21 | 4-chlorophenyl | O | bond | 4-nitrophenyl |
| 22 | 4-methylphenyl | O | bond | 4-hydroxyphenyl |
| 24 | 4-dimethyl-amino-phenyl | O | bond | 3,4,5-tri-methoxy-phenyl |
| 26 | 4-nitro-3-hydroxy-phenyl | O | bond | 3,4,5-trifluoro-phenyl |
| 30 | cyclohexyl | O | prop-2-enyl | 3,4,5-triamino-phenyl |
| 31 | cyclopentyl | O | methyl | 4-hydroxyphenyl |
| 32 | adamantyl | O | ethyl | phenyl |
| 33 | benzyl | O | i-propyl | 9-anthracenyl |
| 34 | 4-hydroxy-benzyl | O | n-propyl | 4-pyrenyl |
| 39 | 2-phenyl-ethenyl | O | bond | 4-sulfonylphenyl |
| 40 | 3-phenylprop-2-enyl | O | chloro-methyl | 4-imino-phenyl |
| 41 | 3-bromopropyl | O | —$CH_2$—N═CH— | 4-phenylethoxy-phenyl |
| 42 | 4-fluoro-b-butyl | O | —$CH_2$—S—$CH_2$— | 4-ethylphenoxy-phenyl |
| 43 | 3-methoxy-propyl | O | —$CH_2$—NH—$CH_2$— | 4-phenoxy-phenyl |
| 44 | 2-hydroxyethyl | O | —$CH_2$—O—$CH_2$— | 3-phenylpropyl-phenyl |
| 46 | tert-butyl | O | bond | 2-chloro-phenyl |
| 47 | tert-butyl | O | bond | 4-chloro-phenyl |
| 48 | tert-butyl | O | bond | 3,4,5-trimethoxy-phenyl |
| 51 | tert-butyl | O | —O—$CH_2$—, X attaches directly to the $CH_2$ | phenyl |
| 52 | methyl | S | bond | 4-bromophenyl |
| 53 | ethyl | S | bond | phenyl |
| 54 | n-propyl | S | bond | 3,4,5-trihydroxy-phenyl |
| 55 | i-propyl | S | bond | 3,4,5-trimethoxy-phenyl |
| 56 | n-butyl | S | bond | 3-hydroxyphenyl |
| 57 | t-butyl | S | bond | 4-nitro-naphthyl |
| 58 | s-butyl | S | bond | 3-hydroxy-napthyl |
| 59 | pentyl | S | bond | benzyl |
| 60 | hexyl | S | bond | 4-ethylphenyl |
| 61 | heptyl | S | bond | 4-ethenylphenyl |
| 65 | 1,1,dimethyl-propyl | S | bond | phenyl |
| 66 | ethenyl | S | bond | cyclohexyl |
| 67 | prop-2-enyl | S | bond | 3-bromo-cyclohexyl |
| 68 | phenyl | S | bond | adamantyl |
| 71 | 4-hydroxy-phenyl | S | bond | 1-naphthyl |
| 72 | 4-chlorophenyl | S | bond | 4-nitrophenyl |
| 73 | 4-methylphenyl | S | bond | 4-hydroxyphenyl |
| 75 | 4-dimethyl-amino-phenyl | S | bond | 3,4,5-trimethyl-phenyl |
| 77 | 4-nitro-3-hydroxy-phenyl | S | bond | 3,4,5-trifluoro-phenyl |
| 81 | cyclohexyl | S | prop-2-enyl | 3,4,5-triamino-phenyl |
| 82 | cyclopentyl | S | methyl | 4-hydroxyphenyl |
| 83 | adamantyl | S | ethyl | phenyl |
| 84 | benzyl | S | i-propyl | 9-anthracenyl |
| 85 | 4-hydroxy-benzyl | S | n-propyl | 4-pyrenyl |
| 90 | 2-phenyl-ethenyl | S | bond | 4-sulfonylphenyl |
| 91 | 3-phenylprop-2-enyl | S | chloro-methyl | 4-imino-phenyl |
| 92 | 3-bromopropyl | S | —$CH_2$—N═CH— | 4-phenylethoxy-phenyl |
| 93 | 4-fluoro-b-butyl | S | —$CH_2$—S—$CH_2$— | 4-ethylphenoxy-phenyl |
| 94 | 3-methoxy-propyl | S | —$CH_2$—NH—$CH_2$— | 4-phenoxy-phenyl |

-continued

| Compound | R | A | D | X |
|---|---|---|---|---|
| 95 | 2-hydroxyethyl | S | —CH$_2$—O—CH$_2$— | 3-phenylpropyl-phenyl |
| 97 | tert-butyl | S | bond | 2-chloro-phenyl |
| 98 | tert-butyl | S | bond | 4-chloro-phenyl |
| 99 | tert-butyl | S | bond | 3,4,5-trimethoxy-phenyl |
| 102 | tert-butyl | S | —O—CH$_2$—, | phenyl |

-continued

| Compound | R | A | D | X |
|---|---|---|---|---|

X attaches directly to the CH$_2$

\* \* \* \* \*